US012773521B2

(12) United States Patent
Squires

(10) Patent No.: US 12,773,521 B2
(45) Date of Patent: Oct. 27, 2026

(54) CATHETER INCLUDING MULTI-LAYER OUTER JACKET

(71) Applicant: Covidien LP, Mansfield, MA (US)

(72) Inventor: Alexander D. Squires, Santa Ana, CA (US)

(73) Assignee: Covidien LP, Mansfield, MA (US)

( * ) Notice: Subject to any disclaimer, the term of this patent is extended or adjusted under 35 U.S.C. 154(b) by 801 days.

(21) Appl. No.: 18/149,433

(22) Filed: Jan. 3, 2023

(65) Prior Publication Data

US 2024/0216644 A1 Jul. 4, 2024

(51) Int. Cl.
*A61M 25/00* (2006.01)

(52) U.S. Cl.
CPC .... *A61M 25/0012* (2013.01); *A61M 25/0045* (2013.01); *A61M 25/005* (2013.01)

(58) Field of Classification Search
CPC .......... A61M 25/0012; A61M 25/0045; A61M 25/005; A61M 25/0054; A61M 25/0053
See application file for complete search history.

(56) References Cited

U.S. PATENT DOCUMENTS 5,951,929 A * 9/1999 Wilson .............. A61M 25/0009 264/296
6,135,992 A 10/2000 Wang
6,197,015 B1 3/2001 Wilson
7,674,411 B2 3/2010 Berg et al.
10,398,874 B2 9/2019 Williams et al.
11,109,920 B2 9/2021 Al-jadda et al.
11,219,740 B2 1/2022 Jackson et al.
11,565,082 B2 1/2023 Yourgenlow et al.
2010/0160862 A1 6/2010 Howat et al.
2020/0297972 A1 9/2020 Yee et al.
2022/0001141 A1 1/2022 Yourgenlow et al.
2022/0008692 A1 1/2022 Pulugurtha et al.

* cited by examiner

*Primary Examiner* — James D Ponton
*Assistant Examiner* — John A Doubrava
(74) *Attorney, Agent, or Firm* — Shumaker & Sieffert, P.A.

(57) ABSTRACT

In some examples, a catheter includes an elongated body defining a longitudinal axis and including an outer jacket. A portion of the outer jacket includes a first layer and a second layer overlying the first layer. The first layer includes a first segment and a second segment longitudinally adjacent to the first segment. The second layer includes a third segment and a fourth segment longitudinally adjacent to the third segment. Each segment includes a transition portion that is not continuous parallel to the longitudinal axis and a core portion that is continuous parallel to the longitudinal axis. A core portion of the second segment overlaps transition portions of the third and fourth segments radially from the longitudinal axis, while a core portion of the third segment overlaps transition portions of the first and second segments radially from the longitudinal axis.

20 Claims, 6 Drawing Sheets

CATHETER INCLUDING MULTI-LAYER OUTER JACKET

TECHNICAL FIELD

This disclosure relates to medical catheters and methods of making the same.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

In some aspects, this disclosure describes example catheters with an outer jacket having a smooth durometer gradient along at least a portion of a length of the catheter, and methods of forming catheters. A durometer of the outer jacket may, for example, increase or decrease along part of or an entire length of the outer jacket. The disclosure describes outer jacket segments configured to achieve any suitable durometer profile along the length of the catheter, including a relatively continuous increase or decrease in the durometer of the outer jacket gradient along the length of the catheter, a sigmoidal durometer gradient of the outer jacket gradient along the length of the catheter, or the like.

In some examples described herein, a catheter includes an inner liner, an outer jacket, and a structural support member positioned between at least a portion of the inner liner and at least a portion of the outer jacket. The outer jacket includes two or more layers in which each layer is formed from a plurality of outer jacket segments. Each outer jacket segment is longitudinally adjacent to another outer jacket segment of a respective layer, and at least two of the outer jacket segments have different durometers. A relatively abrupt change in durometer at a junction or transition between adjacent outer jacket segments of a respective layer may be a relatively weak spot at which the catheter body may be more likely to buckle or kink.

To increase smoothness of a transition in stiffness gradient (e.g., change in stiffness along an axis) of the outer jacket, outer jacket segments within and between the various layers may be shaped and arranged to gradually transition segments with different durometers within a layer and counter transition segments with different durometers between layers. The discrete outer jacket segments of each layer of the outer jacket are shaped and arranged such that transition portions of adjacent segments overlap along an axis of the catheter to produce a gradually varying durometer over the transition portion between the adjacent segments. The various layers of the outer jacket may be positioned longitudinally along the length of the catheter such that the transition portions of each layer are staggered along an axis of the device. For example, a second layer of the outer jacket may be positioned over a first layer of the outer jacket such that transition portions of the outer jacket segments in the first layer overlie non-transition portions of the outer jacket segments of the second layer, and vice versa.

By arranging the layers to stagger the transition portions, the resulting outer jacket may have a relatively smooth change in durometer gradient (e.g., a change in durometer along an axis) compared to outer jackets that are formed from a single layer. For example, a durometer profile (e.g., an average durometer at various points along an axis) of the outer jacket may be an aggregate of the durometer profiles of various layers of the outer jacket, and staggering transition portions having a varying durometer to overlap non-transition portions having a constant durometer may produce a more gradual change in durometer along the axis of the catheter.

The examples described herein may be combined in any permutation or combination.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
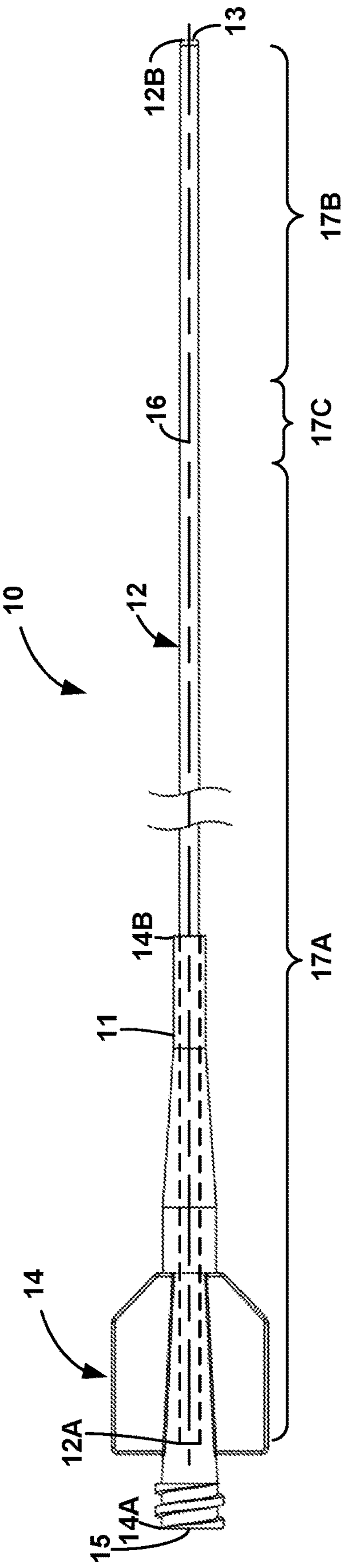
FIG. 1 is a side elevation view of an example catheter, which includes a catheter body and a hub.

The disclosure describes a catheter that includes a relatively flexible catheter body having a multilayer outer jacket that has increased structural integrity compared to a single layer outer jacket and is configured to be navigated through vasculature of a patient. Catheters may be used to diagnose and treat a variety of conditions, including thrombosis. For example, thrombosis occurs when a thrombus (e.g., a blood clot or other embolus) forms and obstructs vasculature of a patient. In some medical procedures, to treat a patient with thrombosis, a clinician may position an aspiration catheter in a blood vessel of the patient (i.e., catheterization) near the thrombus, apply suction to the aspiration catheter, and engage the thrombus with a tip of the aspiration catheter. This medical procedure may be, for example, A Direct Aspiration first Pass Technique (ADAPT) for acute stroke thrombectomy, or any other aspiration of thrombus or other material from the neurovasculature or other blood vessels.

In addition to or instead of medical aspiration, a catheter can be used to deliver a therapeutic device to a target treatment site within vasculature (e.g., neurovasculature) of a patient to treat a defect in the vasculature, such as, but not limited to, aneurysms or arteriovenous malformations. The therapeutic neurovascular device may include any suitable medical device configured to be used to treat a defect in vasculature of a patient or used to facilitate treatment of the neurovasculature. For example, the therapeutic device can include a thrombectomy device, a flow diverter, a stent, an aspiration catheter, a drug delivery catheter, a balloon catheter, a microvascular plug, a filter, an embolic retrieval device (e.g., a stent retriever or an aspiration catheter), or an implantable medical device, such as an embolic coil.

To position a catheter in a blood vessel of a patient, a clinician may push a proximal portion (e.g., a proximal end) of the catheter to advance the catheter through the blood vessel. Walls of the blood vessel may guide a distal tip (e.g., at a distal end) of the catheter through the blood vessel. However, some blood vessels, such as cerebral arteries, have tortuous configurations. These tortuous configurations may include relatively low radius bends that sharply bend the catheter or create resistance along a longitudinal axis of the catheter. As discussed in further detail below, the catheters described herein enable the catheter to be navigated to a target site within vasculature of a patient with relatively high structural integrity e.g., by smoothing transitions in a segmented, multi-layered outer jacket by both longitudinally (i.e., along a longitudinal axis) overlapping transition regions between adjacent segments of the outer jacket and radially (i.e., orthogonal to the longitudinal axis) overlapping the transition regions with non-transition regions between adjacent layers of the outer jacket. As a result, the catheters described herein may resist buckling or kinking in the segmented outer jacket.

In some examples described herein, a catheter body includes an outer jacket positioned around a structural support member and an inner liner. The outer jacket includes two or more layers that each include multiple outer jacket segments. Within each layer of the outer jacket, the outer jacket segments form alternating regions of uniform flexibility within a single segment, such as within a continuous central portion of the segment, and a transition in flexibility between adjacent segments, such as through interfacing tapered ends of the segments (i.e., intra-layer longitudinal overlap). In some examples, the layers of the outer jacket are arranged along and/or around a longitudinal axis such that regions of uniform flexibility within one layer radially (i.e., orthogonal to a longitudinal axis) overlap regions of a transition in flexibility of another layer (i.e., inter-layer radial overlap). The intra-layer longitudinal overlap of the outer jacket segments and inter-layer radial overlap of the transitions between the outer jacket segments may more evenly distribute a change in durometer, and correspondingly a change in stiffness, along a length of the catheter body, such that the catheter body may be less likely to buckle in response to compression or bending forces experienced while navigating the catheter through the vasculature compared to catheters that do not include a multi-layer outer jacket having longitudinally overlapping outer jacket segments and radially overlapping transitions between outer jacket segments.

In some examples, the outer jacket is configured with multiple layers at particular portions of the catheter to smoothly change stiffness at the particular portions of the catheter. For example, certain portions of the catheter may be more likely to experience buckling or kinking than other portions of the catheter, such as due to relatively higher forces or deformation experienced at these portions or reduced inter-coil or inter-braid contact between the inner liner and outer jacket at these portions. The outer jacket may include multiple layers as described above to reinforce such portions of the catheter.

In various ways described herein, example catheters that include a multi-layer outer jacket having a smooth (e.g., low variability of rate of change) durometer gradient may resist temporary (e.g., buckling) or permanent (e.g., delamination) deformation when being navigated through vasculature having tortuous configurations. FIG. 1 is a side elevation view of an example catheter 10, which includes a catheter body 12 and a catheter hub 14. Catheter hub 14 is positioned at a proximal end of catheter 10 and defines an opening through which at least one inner lumen 25 (shown in FIG. 2) of catheter body 12 may be accessed and, in some examples, closed. For example, catheter hub 14 may include a luer connector for connecting to another device, a hemostasis valve, or another mechanism or combination of mechanisms. In some examples, catheter 10 includes strain relief member 11, which may be a part of catheter hub 14 or may be separate from catheter hub 14. In other examples, the proximal end of catheter 10 can include another structure in addition or, or instead of, catheter hub 14.

Catheter body 12 is an elongated body that extends from proximal end 12A to distal end 12B and defines at least one inner lumen 25 (e.g., one inner lumen, two inner lumens, or three inner lumens) that terminates at distal opening 13 defined by catheter body 12. In the example shown in FIG. 1, proximal end 12A of catheter body 12 is received within catheter hub 14 and is mechanically or otherwise connected to catheter hub 14 via an adhesive, welding, or another suitable technique or combination of techniques. Opening 15 defined by catheter hub 14 and located at proximal end 14A of catheter hub 14 is aligned with inner lumen 25 of catheter body 12, such that inner lumen 25 of catheter body 12 may be accessed via opening 15.

Catheter body 12 has a suitable length for accessing a target tissue site within the patient from a vascular access point. The length may be measured along longitudinal axis 16 of catheter body 12. The target tissue site may depend on the medical procedure for which catheter 10 is used. For example, if catheter 10 is a distal access catheter used to access vasculature in a brain of a patient from a femoral artery access point at the groin of the patient, catheter body 12 may have a length of about 129 centimeters (cm) to about 135 cm, such as about 132 cm, although other lengths may be used. In other examples, such as examples in which catheter 10 is a distal access catheter used to access vasculature in a brain of a patient from a radial artery access point, catheter body 12 may have a length of about 80 cm to about 120 cm, such as about 85 cm, 90 cm, 95 cm, 100 cm, 105 cm, although other lengths may be used (e.g., sheaths or radial intermediate catheters may be 5-8 cm longer).

Catheter body 12 can be relatively thin-walled, such that it defines a relatively large inner diameter for a given outer diameter, which may further contribute to the flexibility and kink-resistance of catheter body 12. The wall thickness of catheter body 12 may be the difference between the outer diameter of catheter body 12 and the inner diameter of catheter body 12, as defined by inner lumen 25. For example, in some examples, an outer diameter of catheter body 12 is about 4 French to about 12 French, such as about 5 French or about 6 French. The measurement term French, abbreviated Fr or F, is three times the diameter of a device as measured in mm. Thus, a 6 French diameter is about 2 millimeters (mm), a 5 French diameter is about 1.67 mm, a 4 French diameter is about 1.33 mm, and a 3 French diameter is about 1 mm. The term "about" or "approximately" as used herein with dimensions may refer to the exact numerical value or a range within the numerical value resulting from manufacturing tolerances and/or within 1%, 5%, or 10% of the numerical value. For example, a length of about 10 mm refers to a length of 10 mm to the extent permitted by manufacturing tolerances, or a length of 10 mm+/−0.1 mm, +/−0.5 mm, or +/−1 mm in various examples.

In some examples, at least a portion of an outer surface of catheter body 12 includes one or more coatings, such as, but not limited to, an anti-thrombogenic coating, which may help reduce the formation of thrombi in vitro, an anti-microbial coating, and/or a lubricating coating. The lubricating coating may be configured to reduce static friction and/kinetic friction between catheter body 12 and tissue of the patient as catheter body 12 is advanced through the vasculature. The lubricating coating can be, for example, a hydrophilic coating. In some examples, the entire working length of catheter body 12 (from distal end 14B of hub 14 to distal end 12B) is coated with the hydrophilic coating. In other examples, only a portion of the working length of catheter body 12 coated with the hydrophilic coating. This may provide a length of catheter body 12 distal to distal end 14B of hub 14 with which the clinician may grip catheter body 12, e.g., to rotate catheter body 12 or push catheter body 12 through vasculature.

As described in further detail below, catheter body 12 may be used to access relatively distal locations in a patient, such as the MCA in a brain of a patient. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists and/or turns) through the vasculature to reach these tissue sites. Catheter body 12 may be structurally configured to be relatively flexible, pushable, and kink-, buckle-, and delamination-resistant, so that it may resist buckling when a pushing force is applied to a relatively proximal portion of catheter 10 to advance the catheter body 12 distally through vasculature, resist kinking when traversing around a tight turn in the vasculature, and/or resist delamination and/or layer separation when bending around a tight turn of the vasculature. As one example, kinking or buckling may occur when a weak point of a catheter body, such as a portion of the catheter body that includes a transition between different structures or materials, undergoes deformation along (e.g., buckling) or away from (e.g., kinking) from an axis of the catheter body in response to a bending or compressive force. As another example, delamination may occur when two or more components within a catheter body, such as an inner liner, an outer jacket, a structural support member, and/or a support layer between any of the inner liner, outer jacket, or structural support member, separate in response to a bending or compressive force. Kinking, buckling, and/or delamination of catheter body 12 may hinder a clinician's efforts to push catheter body 12 distally, e.g., past a turn.

A characteristic that may contribute to at least the pushability, flexibility, and/or integrity of catheter body 12 is a local variability in components of catheter body 12, including a local variability of a durometer of the outer jacket. For example, a catheter body may include multiple outer jacket segments that longitudinally abut adjacent outer jacket segments. To at least partially create a varying stiffness of a portion of the catheter body along the length of the portion, various properties of the outer jacket segments, such as a durometer, may be selected to create a durometer gradient (e.g., a durometer that decreases distally or increases distally). The outer jacket segments may each include a single material having a relatively uniform thickness and durometer. A point or section of an outer jacket having an abrupt change in the durometer gradient, such as at a junction between outer jacket segments having dissimilar durometers, may be more susceptible to buckling or kinking.

In examples of catheters described herein, the outer jacket includes two or more layers that each include multiple outer jacket segments. The layers are, for example, radially adjacent to each other, e.g., coaxial layers, and can be referred to as longitudinally extending layers in some examples. Within each layer, the outer jacket includes alternating regions of uniform flexibility corresponding to a single outer jacket segment and variable flexibility corresponding to a transition between adjacent outer jacket segments. The layers of the outer jacket may be arranged such that regions of uniform flexibility within one layer may radially (i.e., perpendicular to a longitudinal axis) overlap regions of variable flexibility of another layer. For example, the regions of uniform flexibility may fully or partially overlap the regions of variable flexibility. The intra-layer longitudinal overlap of the outer jacket segments and inter-layer radial overlap of the transitions between the outer jacket segments may more evenly distribute a change in durometer along a length and around a circumference of the catheter body, such that catheter body 12 may be less likely to buckle in response to compression or bending forces experienced while navigating catheter body 12 through the vasculature compared to catheters that do not include a multi-layer outer jacket having longitudinally overlapping outer jacket segments and radially overlapping transitions between outer jacket segments.

Figure 2:
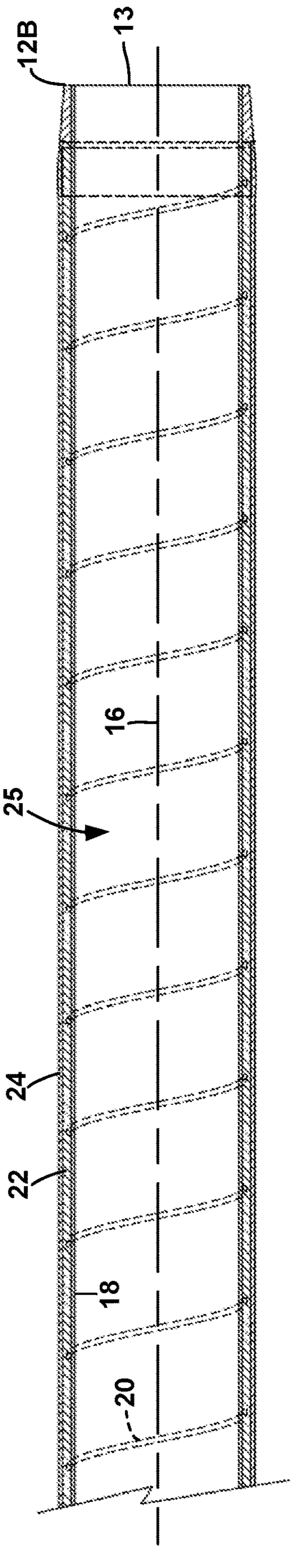
FIG. 2 is a conceptual cross-sectional view of a part of the catheter body of FIG. 1, where the cross-section is taken through a center of the catheter body and along a longitudinal axis of the catheter body.

FIG. 2 is a conceptual cross-sectional view of a part of catheter body 12 including distal end 12B, where the cross-section is taken through a center of catheter body 12 along longitudinal axis 16. As illustrated in the quad-layer configuration of FIG. 2, catheter body 12 includes inner liner 18, structural support member 20, support layer 22, and outer jacket 24; however, in other examples, catheter body 12 may not include structural support member 20 and/or support layer 22, such as in a tri-layer configuration as illustrated in FIG. 3.

Inner liner 18 defines inner lumen 25 of catheter body 12, inner lumen 25 extending from proximal end 12A to distal end 12B and defining a passageway extending from proximal end 12A to distal opening 13 at distal end 12B of catheter body 12. Inner lumen 25 may be sized to receive a medical device (e.g., another catheter, a guidewire, an embolic protection device, a stent, or any combination thereof), a therapeutic agent, or the like. At least the inner surface of inner liner 18 defining inner lumen 25 may be lubricious in order to facilitate the introduction and passage of a device, a therapeutic agent, or the like, through inner lumen 25. For example, the material from which the entire inner liner 18 is formed may be lubricious, or inner liner 18 may be formed from two or more materials, where the material that defines inner lumen 25 may be more lubricious than the material that interfaces with structural support member 20 and support layer 22. In addition to, or instead of, being formed from a lubricious material, an inner surface of inner liner 18 may be coated with a lubricious coating. Example materials from which inner liner 18 may be formed include, but are not limited to, polytetrafluoroethylene (PTFE), fluoropolymer, perfluoroalkyoxy alkane (PFA), fluorinated ethylene propylene (FEP), or any combination thereof. For example, inner liner 18 may be formed from an etched PTFE, e.g., may consist essentially of an etched PTFE.

Structural support member 20 may be configured to increase the structural integrity of catheter body 12 while allowing catheter body 12 to remain relatively flexible. For example, structural support member 20 may be configured to help catheter body 12 substantially maintain its cross-sectional shape or at least help prevent catheter body 12 from buckling or kinking as it is navigated through tortuous anatomy. Structural support member 20, together with inner liner 18, outer jacket 24, and optionally support layer 22, may help distribute both pushing and rotational forces along a length of catheter body 12, which may help prevent kinking of catheter body 12 upon rotation of catheter body 12 or help prevent buckling of catheter body 12 upon application of a pushing force to catheter body 12. As a result, a clinician may apply pushing forces, rotational forces, or both, to proximal portion 17A of catheter body 12, and such forces may cause distal portion 17B of catheter body 12 to advance distally, rotate, or both, respectively. In the example shown in FIG. 2, structural support member 20 extends along only a portion of a length of catheter body 12; however, in other examples, structural support member 20 may extend along an entire length of catheter body 12.

In some examples, structural support member 20 includes a generally tubular braided structure, a coil member defining a plurality of turns (e.g., as illustrated by portion 30 of catheter body 12 in FIG. 3), or a combination of a braided structure and a coil member. Thus, although examples of the disclosure may describe structural support member 20 as a coil, in some other examples, the catheter bodies described herein may include a braided structure instead of a coil or a braided structure in addition to a coil. For example, a proximal portion of structural support member 20 may include a braided structure and a distal portion of structural support member 20 may include a coil member, or vice versa. Structural support member 20 can be made from any suitable material, such as, but not limited to, a metal (e.g., a nickel titanium alloy, stainless steel, tungsten, titanium, gold, platinum, palladium, tantalum, silver, or a nickel-chromium alloy, a cobalt-chromium alloy, or the like), a polymer, a fiber, or any combination thereof. In some cases, a nickel titanium alloy may be more crush resistant than stainless steel, and, therefore, may be used to form a structural support member 20 of a catheter that is more resistant to kinking and buckling compared to stainless steel. In some examples, structural support member 20 includes one or more metal wires braided or coiled around inner liner 18. The metal wires may include round wires, flat-round wires, flat wires, or any combination thereof.

In the example illustrated in FIG. 2, structural support member 20 is formed from a wire, such as a rounded (in cross-section) wire, that is shaped to define a coil. In other examples, member 20 may be formed, at least in part, from a flat (in cross-section) wire that is shaped to define a coil. A rounded wire may define a coil member having a lower surface area than a flat wire, such that, for a given length of structural support member 20, inner liner 18 and/or outer jacket 24 may have a higher contact area between coils of structural support member 20. A flat wire may define a coil member having a higher surface area than a round wire, such that, for a given length of structural support member 20, structural support member 20 may have a higher contact area with inner liner 18 and/or outer jacket 24.

In examples in which structural support member 20 includes a coil (e.g., a helical coil), the flexibility of structural support member 20 may be, at least in part, a function of a pitch of the coil. For a given wire, a larger pitch results in larger gaps between adjacent turns of the wire forming member 20 and a higher degree of flexibility. The pitch can be, for example, the width of one complete turn of wire, measured in a direction along longitudinal axis 16. In some examples, a pitch of structural support member 20 varies along a length of structural support member 20, such that a stiffness (or flexibility) varies along the length. The pitch may continuously vary along the length of member 20, or may progressively change, e.g., include different sections, each section having a respective pitch.

Structural support member 20 may be coupled, adhered, and/or mechanically connected to at least a portion of an outer surface of inner liner 18 and/or at least a portion of an inner surface of outer jacket 24. In some examples, structural support member 20 may be directly coupled, adhered, and/or mechanically connected to at least a portion of an outer surface of inner liner 18 and/or at least a portion of an inner surface of outer jacket 24. For example, while catheter 10 of FIG. 2 illustrates a quad-layer configuration that includes support layer 22, in some examples, such as illustrated in portion 30 of FIG. 3, catheter 10 may include a tri-layer configuration that does not include support layer 22. In such examples, the inner surface of outer jacket 24 and the outer surface of inner liner 18 may, at least partly, directly contact and/or adhere to each other between braids or coils of structural support member 20.

In other examples, such as illustrated in FIG. 2, structural support member 20 may be indirectly coupled, adhered, and/or mechanically connected to at least a portion of the outer surface of inner liner 18 and/or at least a portion of the inner surface of outer jacket 24 via support layer 22. For example, support layer 22 may be a thermoplastic material or a thermoset material, such as a thermoset polymer and/or a thermoset adhesive. In some examples, support layer 22 is positioned between the entire length of structural support member 20 and inner liner 18, while in other examples, support layer 22 is only positioned between a part of the length of structural support member 20 and inner liner 18.

Outer jacket 24 is positioned radially outward of inner liner 18 and structural support member 20, and, in some examples, defines an outer surface of catheter body 12. Although a coating or another material may be applied over the outer surface of outer jacket 24, outer jacket 24 may substantially define a shape and size of the outer surface of catheter body 12. In example catheters that do not include support layer 22, such as illustrated in FIG. 3, outer jacket 24 may be configured to fill at least part of the spaces (e.g., part or all of the spaces) between portions of structural support member 20, e.g., the spaces between turns of structural support member 20 in examples in which member 20 is a coil member or the spaces defined between pics of a braid. In example catheters that include support layer 22, support layer 22 may be configured to fill at least part of the spaces between portions of structural support member 20.

In some instances, the presence of outer jacket 24 and/or support layer 22 between turns of member 20 may help adhere outer jacket 24 and inner liner 18 to each other and securely integrate structural support member 20 into catheter body 12, such that structural support member 20 may resist detachment during bending or compression of catheter 10. For example, at least by minimizing or even eliminating voids between turns of structural support member 20, such as may be caused by insufficient flow of a material of outer jacket 24, outer jacket 24 and/or support layer 22 may provide a higher contact surface between inner liner 18 and outer jacket 24, which may better distribute pushing or torquing forces applied to proximal portion 17A of catheter body 12 to distal portion 17B. In addition or instead, minimizing or even eliminating voids between turns of structural support member 20 may provide longitudinal support to structural support member 20 to secure structural support member within catheter body 12.

In some instances, the presence of outer jacket 24 and/or support layer 22 between turns of member 20 may help distribute the flexibility provided by structural support member 20 along the length of structural support member 20, which may help prevent catheter body 12 from kinking. For example, at least by eliminating voids between turns of structural support member 20, outer jacket 24 and/or support layer 22 may transfer the flexing motion from structural support member 20 along a length of catheter body 12. In some examples, support layer 22 has a thickness (measured in a direction orthogonal to longitudinal axis 16) that is greater than or equal to a cross-sectional dimension of the wire that forms the member 20, such that layer 22 is at least partially positioned between outer jacket 24 and structural support member 20. In other examples, support layer 22 has a thickness that is less than or equal to a cross-sectional dimension of the wire that forms the structural support member 20, such that support layer 22 is not positioned between outer jacket 24 and structural support member 20.

Outer jacket 24, together with structural support member 20 and inner liner 18, may be configured to define catheter body 12 having the desired flexibility, kink resistance, and pushability characteristics. Outer jacket 24 may have stiffness characteristics that contribute to a desired stiffness profile (i.e., a spatially varying stiffness along and/or around an axis) of catheter body 12. For example, outer jacket 24 may be formed to have a durometer that decreases from a proximal portion 17A of catheter body 12 to a distal portion 17B. The stiffness of outer jacket 24 may be, at least in part, a function of a composition, a hardness (e.g., durometer), and/or a thickness of outer jacket 24. For example, a higher durometer may result in less compressibility and a lower degree of flexibility. In some examples, outer jacket 24 is formed from two or more different materials, different thicknesses of materials, or different durometers of materials that enable outer jacket 24 to exhibit the desired stiffness characteristics, such as may described further in FIG. 3A below.

To configure catheter body 12 with a particular stiffness profile (e.g., a stiffness along longitudinal axis 16), outer jacket 24 includes multiple layers that each include multiple outer jacket segments that include varied durometers and are shaped and positioned to produce a relatively smooth transition in stiffness along a length of part of or the entire length of outer jacket 24. Each layer of outer jacket 24 has a varying durometer (e.g., gradual increase or decrease distally, sigmoidally, or other durometer profiles along the length of outer jacket 24), and the relative arrangement of outer jacket segments between layers help make changes in the varying durometer more smooth compared to an outer jacket that includes a single layer.

In some examples, outer jacket 24 has a smooth transition in durometer ("durometer gradient") along longitudinal axis 16. A transition in durometer gradient may present as a spatial rate of change of durometer of outer jacket 24 along longitudinal axis 16. For example, a smooth transition in durometer gradient of outer jacket 24 may present as smaller deviations of the spatial rate of change of the durometer of outer jacket 24 over a particular length of catheter body 12 compared to an outer jacket that includes a single layer of outer jacket having step changes in durometer. As will be described further in FIG. 3D below, the spatial rate of change of durometer may correspond to a local slope of a durometer of outer jacket 24 along longitudinal axis 16 (i.e., a change in durometer over a change in longitudinal position along longitudinal axis 16).

Increased smoothness of a transition in durometer of outer jacket 24 may be measured and/or quantified directly (e.g., durometer) or indirectly (e.g., properties related to durometer) in one or more of a variety of ways including, but not limited to, smooth durometer profile of outer jacket 24 (e.g., average durometer of materials of outer jacket 24, as measured at various points along longitudinal axis 16), staggered transition in durometer of individual layers of outer jacket 24 (e.g., durometer of materials of a layer of outer jacket 24, as measured at various points along longitudinal axis 16), smooth transition in flexibility profile of outer jacket 24 (e.g., degree of outer jacket 24 bending in response to a bending force, as measured at various points along longitudinal axis 16), increased flexibility and kink resistance of catheter body 12 (e.g., presence or degree of catheter body 12 bending in response to a bending force, as measured along various points along longitudinal axis 16), or the like.

In some examples, one or more particular portions of outer jacket 24 have a smooth durometer gradient to reduce buckling of catheter body 12 at the one or more particular portions. For example, these one or more portions that include a smooth durometer gradient can be certain portions of outer jacket 24 that may be more likely to experience stresses that can cause buckling of catheter body 12 than other portions of outer jacket 24.

Figure 3A:
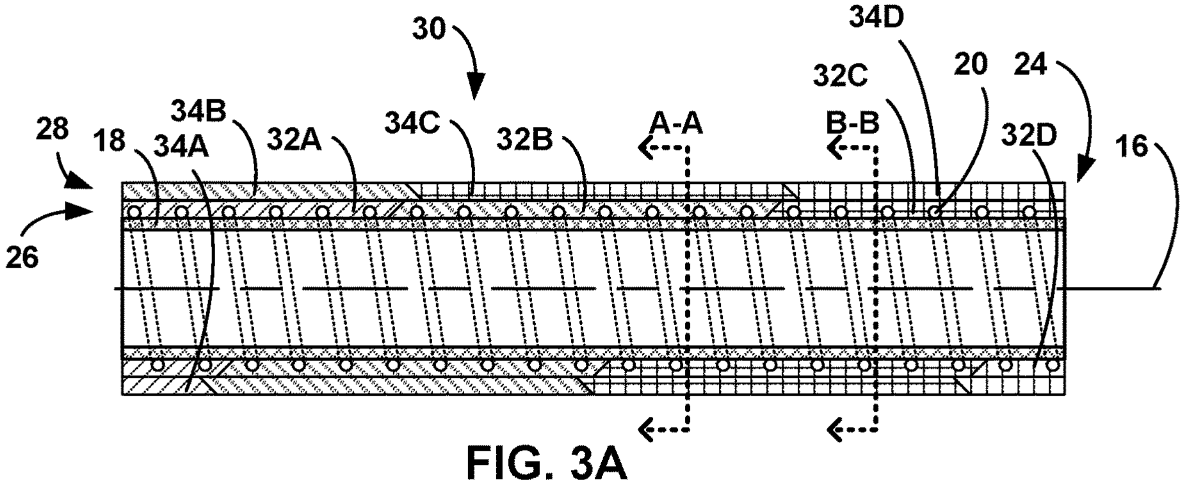
FIG. 3A is a conceptual cross-sectional view of a part of an example catheter body, where the cross-section is taken through a center of the catheter body and along a longitudinal axis of the catheter body.

FIG. 3A is a conceptual cross-sectional view of a portion 30 of a part of an example catheter body (e.g., catheter body 12 of FIG. 2), where the cross-section is taken through a center of the catheter body and along the longitudinal axis (e.g., longitudinal axis 16 in FIG. 1) of the catheter body. While catheter body 12 is primarily referred to in the description of FIG. 3A, in other examples, portion 30 can be a portion of another catheter body. In the example shown in FIG. 3A, portion 30 of catheter body 12 includes inner liner 18, outer jacket 24, and structural support member 20.

Outer jacket 24 includes a plurality of outer jacket layers 26, 28 arranged concentrically around longitudinal axis 16. In the example of FIG. 3A, only a first layer 26 and a second layer 28 are illustrated; however, outer jacket 24 can include any number of two or more layers. In portion 30, first layer 26 overlies inner liner 18 and structural support member 20, and second layer 28 overlies first layer 26. Outer jacket layers 26, 28 are radially adjacent to each other. For example, outer jacket layer 26 is radially inwards of outer jacket layer 28. Outer jacket layers 26, 28 may have a same length and alignment along axis 16 to be fully coextensive, or may have different lengths or a different alignment along axis 16 to be partially coextensive.

Each layer 26, 28 includes a respective plurality of outer jacket segments 32, 34. While illustrated as being discrete segments, outer jacket segments 32, 34 may have any degree of mechanical connection, including as mechanically discrete segments (e.g., prior to reflowing a corresponding sleeve) or as visually indiscrete segments (e.g., after reflowing a corresponding sleeve). For example, outer jacket segments 32, 34 may be visually indiscrete, but may be differentiated by a region of layer 26, 28 having a particular composition or durometer, such as may be determined by measuring a sample. Further, interfaces between segments

32, 34 may include a short transition that may form due to a method used to mechanically connect segments 32, 34, such as due to reflow.

Figure 3B:
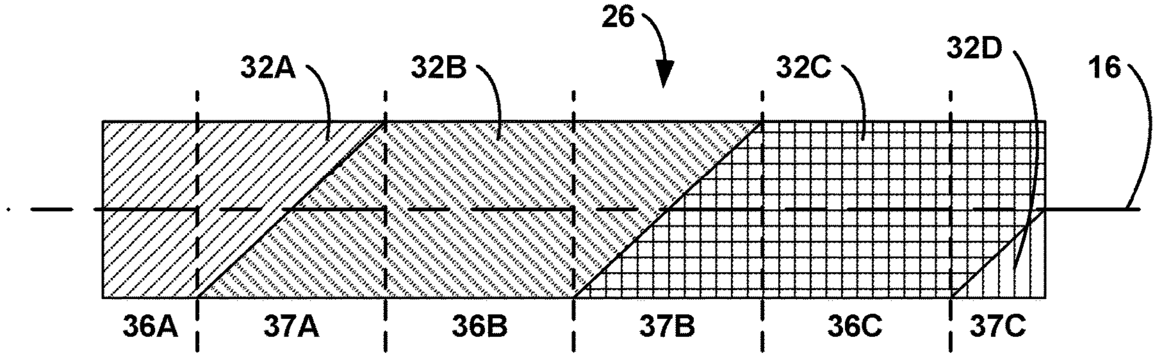
FIG. 3B is a conceptual side view of an example first layer of an outer jacket of the part of the catheter body of FIG. 3A.
Figure 3C:
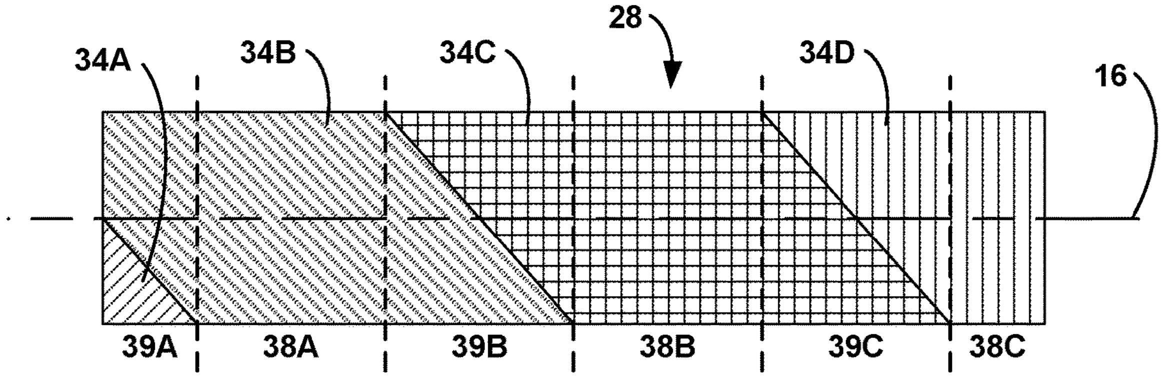
FIG. 3C is a conceptual side view of an example second layer of an outer jacket of the part of the catheter body of FIG. 3A.

FIG. 3B is a conceptual side view of first layer 26 of outer jacket 24 of portion 30 of FIG. 3A, while FIG. 3C is a conceptual side view of second layer 28 of outer jacket 24 of portion 30 of FIG. 3A. First layer 26 includes a first plurality of outer jacket segments 32A. 32B, 32C. 32D, while second layer 28 includes a second plurality of outer jacket segments 34A, 34B, 34C, 34D (collectively referred to herein as "segments 32" or "segments 34," or generally referred to as "segments 32, 34"). In the example of FIGS. 3A-3C, only a first outer jacket segment 32A, a second outer jacket segment 32B, a third outer jacket segment 32C, and a fourth outer jacket segment 32D of the first layer 26 and a first outer jacket segment 34A, a second outer jacket segment 34B, a third outer jacket segment 34C, and a fourth outer jacket segment 34D are illustrated; however, each layer 26, 28 of outer jacket 24 can include any suitable number of outer jacket segments 32 or 34, respectively. Segments 32, 34 can each be, for example, formed from sleeves (e.g., tubular sleeves) that are configured to be positioned over inner liner 18 and structural support member 20, and, if present, support layer 22, as will be described further in FIGS. 4A, 4B, and 5.

Within a respective layer 26, 28, the respective segments 32, 34 are situated longitudinally adjacent to each other, e.g., in an abutting relationship, and, in some examples, can be mechanically connected together to define the respective layer 26, 28 of outer jacket 24 using any suitable technique, such as by welding, an adhesive, heating/reflow, or any combination thereof. Segments 32, 34 may each have any suitable length, which may be selected based on the desired flexibility profile of catheter body 12, such as will be described further in FIGS. 4A and 4B. In some examples, proximal, distal, and intermediate portions 17A-17C (FIG. 1) of catheter body 12 may have their own respective outer jacket segments 32, 34 that each begin and end at the proximal and distal ends of the corresponding catheter body portions 17A-17C. In other examples, one of outer jacket segments 34 may extend at least over both proximal portion 17A and intermediate portion 17C, and/or over both intermediate portion 17C and distal portion 17B.

As described in FIG. 2 above, the stiffness and/or hardness (e.g., durometer) of outer jacket 24 contributes to the flexibility and structural integrity of catheter body 12. Accordingly, the composition and properties of each of segments 32, 34, such as durometer and/or thickness, may be selected to assist in providing portion 30 of catheter body 12 with the desired flexibility characteristics along a length of catheter body 12.

In some examples, the composition of each of segments 32, 34 may be selected to provide catheter body 12 with the desired flexibility characteristics. For example, different materials may have different properties, such as durometer, compressibility, elasticity, and the like. In some examples, at least two outer jacket segments 32, 34 are formed from different materials (e.g., materials having different chemical compositions and/or different material characteristics). Example materials for segments 34 include, but are not limited to, polymers, such as a polyether block amide (e.g., PEBAX®, commercially available from Arkema Group of Colombes, France), an aliphatic polyamide (e.g., Grilamid®, commercially available from EMS-Chemie of Sumter, South Carolina), another thermoplastic elastomer or other thermoplastic material, or combinations thereof.

In some examples, the durometers of each of segments 32, 34 may be selected to help provide catheter body 12 with the desired flexibility characteristics. For example, in some examples, at least two outer jacket segments 32 have different durometers and/or at least two outer jacket segments 34 have different durometers. In some examples, segments 32, 34 may have a durometer between about 30A-100 A or 25D and about 90D. In other examples, however, one or more of the segments 34 may have other hardness values. The hardness of the segments 32, 34 may be selected to obtain more or less flexibility, torqueability, and pushability for all or part of catheter body 12.

In some examples of the catheter body shown in FIGS. 3A-3C, each segment 32, 34 of the respective layers 26, 28 has a different durometer. Each layer 26, 28 may include respective segments 32, 34 arranged to produce alternating regions of uniform durometer and transition in durometer.

For first layer 26, regions of uniform durometer ("core regions") may include portions of layer 26 in which a segment does not longitudinally overlap with a longitudinally adjacent segment 32, while regions of transition in durometer ("transition regions") may include portions of layer 26 in which two adjacent segments 32 longitudinally overlap. Referring to FIG. 3B, first layer 26 includes first outer jacket segment 32A having a first durometer, second outer jacket segment 32B having a second durometer, different from the first durometer, third outer jacket segment 32C having a third durometer, different from the second durometer, and fourth outer jacket segment 32D having a fourth durometer, different from the third durometer. As a result, first layer 26 includes a first core region 36A of a uniform first durometer, a second core region 36B of a uniform second durometer, and a third core region 36C of a uniform third durometer (collectively, "core regions 36"), as well as a first transition region 37A of a transition between the first durometer and the second durometer, a second transition region 37B of a transition between the second durometer and the third durometer, and a third transition region 37C of a transition between the third durometer and the fourth durometer (collectively, "transition regions 37").

Similarly, for second layer 28, core regions may include portions of layer 28 in which a segment does not longitudinally overlap with a longitudinally adjacent segment 34, while transition regions may include portions of layer 28 in which two adjacent segments 34 longitudinally overlap. Referring to FIG. 3C, second layer 28 includes first outer jacket segment 34A having the first durometer, second outer jacket segment 34B having the second durometer, third outer jacket segment 32C having the third durometer, and fourth outer jacket segment 32D having the fourth durometer. As a result, second layer 28 includes a first core region 38A of uniform first durometer, a second core region 38B of uniform second durometer, and a third core region 38C of uniform third durometer (collectively, "core regions 38"), as well as a first transition region 39A of a transition between the first durometer and the second durometer, a second transition region 39B of a transition between the second durometer and the third durometer, and a third transition region 39C of a transition between the third durometer and the fourth durometer (collectively, "transition regions 39").

Figure 3D:
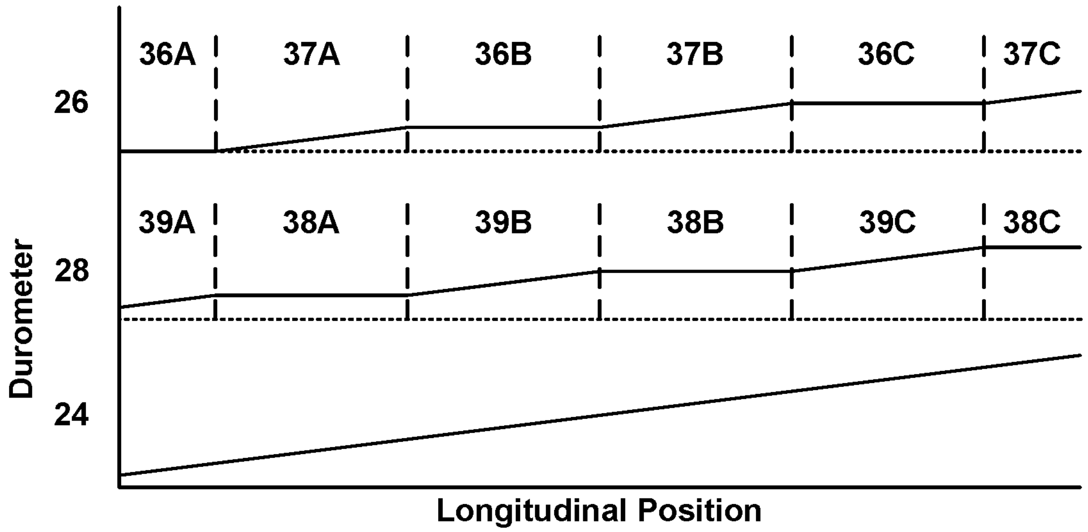
FIG. 3D is a conceptual graph of stiffness as a function of axial length for the part of the catheter body of FIG. 3A.

FIG. 3D is a conceptual graph of durometer as a function of longitudinal position (i.e., "durometer profile") for first layer 26, second layer 28, and outer jacket 24 of portion 30 of FIG. 3A. While the example of FIG. 3D illustrates transitions between segments as producing a durometer profile characterized by a progressively and linearly increasing stiffness in a proximal direction along axis 16, segments 32, 34 may be selected and arranged to produce a durometer profile having any shape, including an increasing durometer, decreasing durometer, varying increasing and/or decreasing durometer, linear change in durometer, non-linear change in durometer, or any combination. A sinusoidal durometer profile is an example of a varying increasing and/or decreasing durometer profile.

First layer 26 defines a first durometer profile that includes core regions 36 having a uniform durometer interspersed with transition regions 37 having an increasing durometer, while second layer 28 defines a second durometer profile that includes core regions 38 having a uniform durometer interspersed with transition regions 39 having an increasing durometer. First layer 26 and second layer 28 may be longitudinally arranged relative to each other, such that each core region 36 of first layer 26 overlaps a transition region 39 of second layer 28, and each core region 38 of second layer 28 overlaps a transition region 37 of first layer 26. As a result, first layer 26 and second layer 28 may define a durometer profile of outer jacket 24 that includes durometer gradient having a smooth transition along longitudinal axis 16 of portion 100. For example, the durometer profile of outer jacket 24 may generally correspond to an aggregate of the durometer profile of first layer 26 and the durometer profile of second layer 28.

In some examples, a smooth durometer gradient is a change in durometer along longitudinal axis 16 that does not include a step change of durometer. For example, first layer 26 may define a change in durometer of first layer 26 along longitudinal axis 16 that includes alternating regions of a uniform durometer and a transition in durometer. Second layer 28 may define a change in durometer of second layer 28 along longitudinal axis 16 that includes alternating regions of a uniform durometer and a transition in durometer. These changes in durometer of first layer 26 and second layer 28 define a smooth change in durometer along longitudinal axis 16 of the portion of outer jacket 24, such that no change in durometer of outer jacket 24 has a step change between a first durometer and second durometer. Instead, each change in durometer is a ramped change, in which at least the first layer or the second layer is gradually increasing in durometer at a given position along longitudinal axis 16.

Figure 3E:
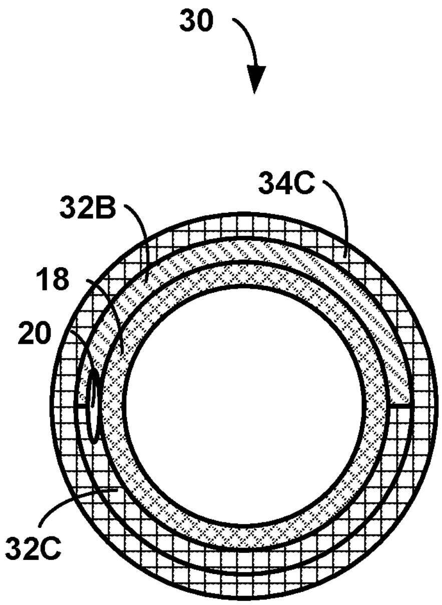
FIG. 3E is a conceptual cross-sectional view of the catheter body of FIG. 3A taken along line A-A in FIG. 3A.
Figure 3F:
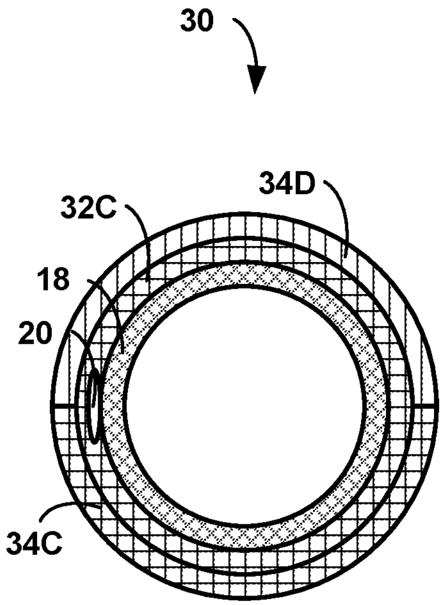
FIG. 3F is a conceptual cross-sectional view of the catheter body of FIG. 3A taken along line B-B in FIG. 3A.

In addition to being longitudinally arranged relative to each other, layers 26, 28 may be tangentially (i.e., around axis 16) arranged such that layers 26, 28 produce a relatively balanced overall durometer around axis 16. FIG. 3E is a conceptual cross-sectional view of portion 30 of the catheter body of FIG. 3A taken along line A-A in FIG. 3A, while FIG. 3F is a conceptual cross-sectional view of portion 30 of the catheter body of FIG. 3A taken along line B-B in FIG. 3A. While each layer 26, 28, may be generally symmetrical around axis 16, each layer 26, 28 may have a slightly average durometer on one side of axis 16 that includes a leading transition than another side of axis 16 that includes a trailing transition. For example, for a segment 32, 34 having a parallelogram side profile, a tangential position corresponding to a leading point may be associated with a higher or lower overall durometer than a tangential position corresponding to a trailing point.

In some examples, layers 26, 28 may be tangentially arranged such that an orientation of a transition direction of transition regions 37, 39 generally oppose each other. For example, in the two-layer configuration illustrated in FIGS. 3E and 3F, a durometer at a tangential point around each layer 26, 28 may vary. In FIG. 3E, a durometer on an "upper" portion of layer 26, including second outer jacket segment 32B, may be higher than a durometer of a "lower" portion of layer 26, including third outer jacket segment 32C, such that layer 26 has an upper-to-lower transition direction. Conversely, in FIG. 3F, a durometer on an "upper" portion of layer 28, including fourth outer jacket segment 34D, may be lower than a durometer of a "lower" portion of layer 28, including third outer jacket segment 34C, such that layer 28 has a lower-to-upper transition direction. In the two-layer outer jacket configuration of FIGS. 3A-3F, such the opposing(180°) orientation of the transition directions may balance the slightly higher overall durometer of each layer 26, 28 at different tangential positions around axis 16. In a three-layer outer jacket configuration, the three layers may be orientated at 120 orientations.

As another example, as illustrated in FIGS. 3B and 3C, segments 32 may be arranged such that an interface between segments 32 intersects longitudinal axis 16 in a first direction (e.g., top-right to bottom-left), while segments 34 may be arranged such that an interface between segments 34 intersects longitudinal axis 16 in a second, opposing direction (e.g., top-left to bottom-right). As a result, an overall stiffness of outer jacket 24 may be relatively uniform at different tangential positions around outer jacket 24, despite having an asymmetrical configuration across longitudinal axis 16.

In some examples, segments 32, 34 may be shaped such that a transition direction may vary between tangential positions, such as by 180°. 120°, 90°, or any other variation. For example, segments 32, 34 may have a trapezium side profile, in which a transition direction of a segment reverses based on whether the transition is at a proximal or distal end of segment 32, 34, may have a more even tangential distribution of durometer at various longitudinal positions of portion 30.

In some examples, such as example portions of catheter body 12 in which catheter body 12 increases in flexibility and/or decreases in stiffness from proximal end 12A towards distal end 12B, the durometer of two longitudinally adjacent outer jacket segments 32, 34 (within a respective layer 26, 28) may decrease in a direction from a proximal end of outer jacket 24 towards a distal end. For example, referring to FIG. 3B, a durometer of second outer jacket segment 32B may be greater than a durometer of first outer jacket segment 32A, and a durometer of third outer jacket segment 32C may be greater than a durometer of second outer jacket segment 32B. In some examples, an average of a durometer of first layer 26 and a durometer of second layer 28 decreases from a proximal end 12A towards distal end 12B. For example, while each layer 26, 28, may have variation along a length, an average of layers 26, 28 may steadily decrease from proximal end 12A to distal end 12B. As a result, catheter body 12 may be more flexible for navigating catheter 10 through vasculature of a patient compared to catheter bodies that have outer jackets with a uniform durometer along the outer jacket length.

In some examples, such as example portions of catheter body 12 in which catheter body 12 decreases in flexibility and/or increases in stiffness along any part of catheter body 12 between from proximal end 12A towards distal end 12B, the durometer of two adjacent outer jacket segments 34 may increase in a direction from a proximal end of outer jacket 24 towards a distal end. For example, referring to FIG. 3B, a durometer of first outer jacket segment 32A may be greater than a durometer of second outer jacket segment 32B. While it may be desirable in some cases to provide a catheter body 12 having a relatively flexible distal portion, as explained above, increasing the durometer of a distal-most section of outer jacket 24 relative to a more proximal section that is directly adjacent to the distal-most section, may provide certain advantages. For example, increasing the durometer of the distal-most section may configure distal opening 13 of catheter body 12 to resist geometric deformation when distal opening 13 (FIG. 1) of catheter body 12 is engaged with a guidewire, which may help support the navigation of catheter body 12 through vasculature. The distal-most section of outer jacket 24 that exhibits the increased stiffness may be a relatively small length of catheter body 12 and, therefore, may not affect the overall flexibility of catheter body 12.

During navigation of catheter 10 through vasculature of a patient, bending of catheter body 12 may exert compressive forces on an inside radius of catheter body 12, such as at portion 30. Without outer jacket 24 having a change in flexibility that has a low variability, the compressive forces may cause portion 30 to kink or buckle at transitions between segments 32 and segments 34. However, a change in flexibility of outer jacket 24 having a smooth or gradual transition in flexibility may more evenly distribute forces to reduce kinking or buckling.

Figure 4A:
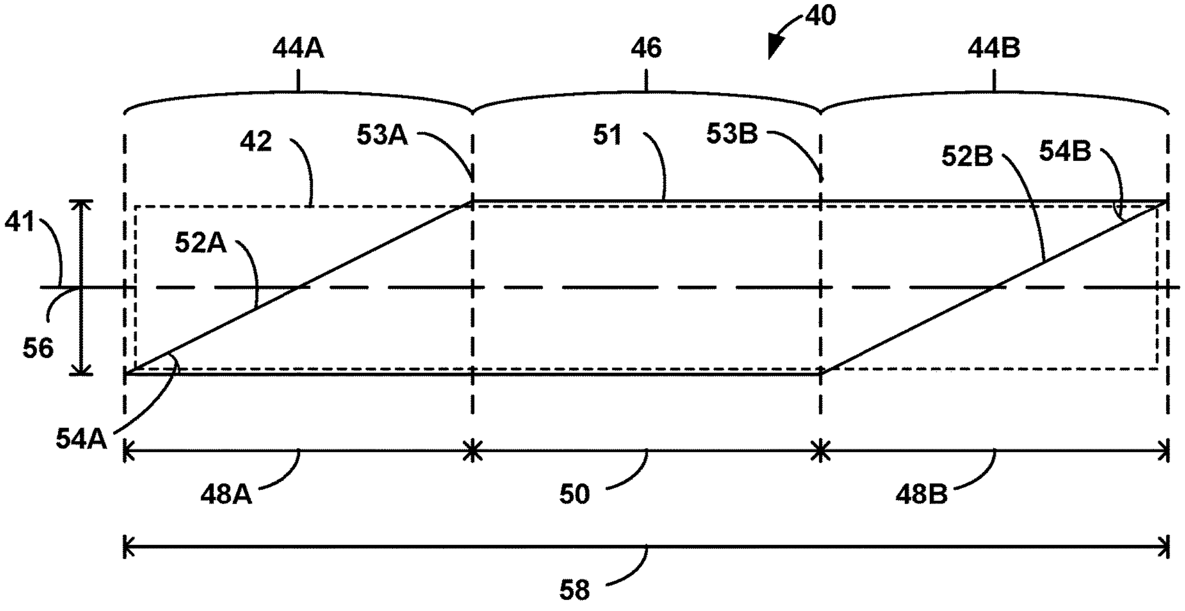
FIG. 4A is a conceptual side view of a segment of an example first layer of an outer jacket of a catheter body.
Figure 4B:
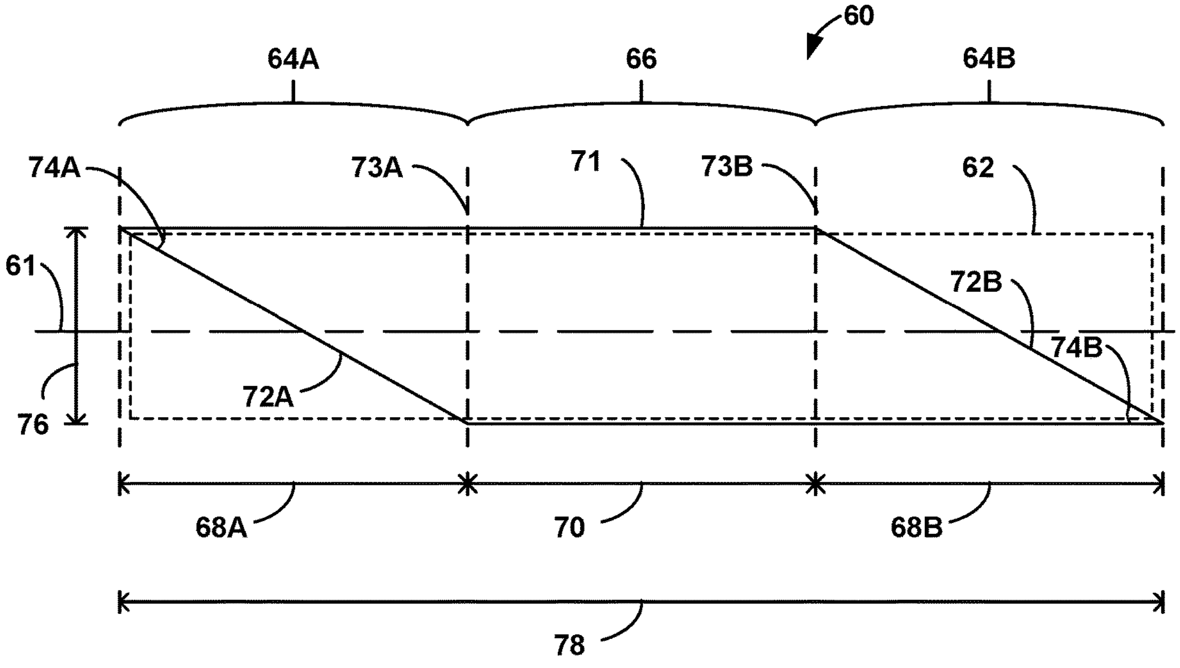
FIG. 4B is a conceptual side view of a segment of an example second layer of an outer jacket of a catheter body.

Segments forming an outer jacket, such as segments 32, 34 described in FIGS. 3A-3D, may be shaped such that, when arranged in a layer, such as layer 26, 28 described in FIGS. 3A-3D, the segments may produce an outer jacket having a relatively smooth transition in durometer along a length of the outer jacket. For example, each of segments 32, 34 may be present on a subassembly of a catheter as a sleeve prior to being mechanically interconnected into a layer 26, 28 of outer jacket 24. FIGS. 4A and 4B describe example segments having a tubular structure and a parallelogram shape from a side profile. However, segments may include a variety of shapes, including a trapezium shape from a side profile, or another shape having sides parallel to a longitudinal axis and one or more sides intersecting the longitudinal axis in a non-orthogonal plane.

FIG. 4A is a conceptual side view of an example sleeve 40 corresponding to an example segment of a first layer of an outer jacket of a catheter body, such as a segment 32 of first layer 26 of outer jacket 24 described in FIG. 3B. Sleeve 40 defines a longitudinal axis 41 and is positioned over one or more components 42, such as an inner liner, a support layer, a structural support member, and/or a mandrel used as part of the catheter manufacturing process. While not fully shown in the side view perspective of FIG. 4A, sleeve 40 includes an outer wall 51 having a tubular shape around axis 41 that defines a lumen and an outer diameter 56, and has an overall length 58.

FIG. 4B is a conceptual side view of a sleeve 60 corresponding to a segment of a second layer of an outer jacket of a catheter body, such as a segment 34 of second layer 28 of outer jacket 24 described in FIG. 3C. Sleeve 60 defines a longitudinal axis 61 and is positioned over a segment of a first layer, such as sleeve 40 described in FIG. 4A. While not fully shown in the side view perspective of FIG. 4B, sleeve 60 includes an outer wall 71 having a tubular shape around axis 61 that defines a lumen and an outer diameter 76 and has an overall length 78.

Sleeves for forming segments of an outer jacket, such as sleeves 40, 60, include at least one transition portion configured to interface with and longitudinally overlap an adjacent sleeve and at least one core portion configured to not longitudinally overlap an adjacent sleeve. Each transition portion of a sleeve is shaped to interface with a transition portion of a longitudinally adjacent sleeve of the respective outer jacket layer and taper an amount of material contributed by the particular sleeve at a longitudinal position. For example, for two longitudinally adjacent sleeves arranged along a longitudinal axis and having different durometers, an average durometer at a particular point along the longitudinal axis may change based on a relative amount of material of a first sleeve and a material of a second sleeve.

In the example of FIG. 4A, sleeve 40 includes one core portion 46 and two transition portions 44A and 44B (collectively, "transition portions 44"). In the example of FIG. 3A, each core portion 46 may correspond to a core region 36 of layer 26, while two transition portions 44 of longitudinally adjacent sleeves may correspond to a transition region 37 of layer 26. Core portion 46 may be defined by a continuous portion of outer wall 51 parallel to axis 41 and having a length 50 parallel to axis 41. Core portion 46 may have a relatively uniform durometer and thickness of outer wall 51 (e.g., uniform or nearly uniform to the extent permitted by manufacturing tolerances).

Sleeve 40 includes a proximal transition portion 44A in a proximal direction from core portion 46 (e.g., toward a proximal end of an elongated body) and a distal transition portion 44B in a distal direction from core portion 46 (e.g., toward a distal end of an elongated body). Proximal transition portion 44A includes a portion of outer wall 51 parallel to axis 41 and a beveled edge 52A of outer wall 51 that is not parallel to axis 41, and forms an angle 54A with the portion of outer wall 51 parallel to axis 41. Similarly, distal transition portion 44B includes a portion of outer wall 51 parallel to axis 41 and a beveled edge 52B of outer wall 51 that is not parallel to axis 41, and form an angle 54B with the portion of outer wall 51 parallel to axis 41. Angles 54A and 54B of respective beveled edges 52A and 52B are configured such that beveled edges 52A and 52B contact and fit with (e.g., mate with) outer jacket segments longitudinally adjacent to sleeve 40. For example, angles 54A and 54B can be selected such that the transition portion 44A of one sleeve 40 abuts transition portion 44B of a longitudinally adjacent sleeve 40.

In the example of FIG. 4B, sleeve 60 includes one core portion 66 and two transition portions 64A and 64B. In the example of FIG. 3A, each core portion 66 may correspond to a core region 38 of layer 28, while two transition portions 64 of adjacent sleeves may correspond to a transition region 39 of layer 28. Core portion 66 may be defined by a continuous portion of outer wall 71 parallel to axis 61 and having a length 70 parallel to axis 61. Core portion 66 may have a relatively uniform durometer and thickness of outer wall 71.

Sleeve 60 includes a proximal transition portion 64A proximal to core portion 66 and a distal transition portion 64B distal to core portion 66 (collectively, "transition portions 64"). Proximal transition portion 64A includes a portion of outer wall 71 parallel to axis 61 and a beveled edge 72A of outer wall 71 that is not parallel to axis 61, and forms an angle 74A with the portion of outer wall 71 parallel to axis 61. Similarly, distal transition portion 64B includes a portion of outer wall 71 parallel to axis 61 and a beveled edge 72B of outer wall 71 that is not parallel to axis 61, and form an angle 74B with the portion of outer wall 71 parallel to axis 61. Angles 74A and 74B of respective beveled edges 72A and 72B are configured such that beveled edges 72A and 72B interface with, contact, and fit with (e.g., mate with) segments longitudinally adjacent to sleeve 60. For example, angles 74A and 74B can be selected such that the transition portion 64A of one segment 60 abuts transition portion 64B of a longitudinally adjacent segment 60.

Referring to both FIG. 4A and FIG. 4B, each transition portion 44, 64 may be differentiated from a respective core portion 46, 66 by a square edge perpendicular to axis 41, 61.

Each core portion 46, 66 may be defined by a tubular portion of the respective sleeve (or segment) bounded by two square edges. For example, core portion 46 is bounded by a proximal square edge 53A and a distal square edge 53B, while core portion 66 is bounded by a proximal square edge 73A and a distal square edge 73B. Between square edges 53, 73, this tubular portion is continuous parallel to a respective axis 41, 61. Each transition portion 44, 64 may be defined by a beveled portion of the respective sleeve (or segment) bounded by a respective beveled edge 52, 72 and a square edge. For example, distal transition portion 44A is bounded by beveled edge 52A and proximal square edge 53A, proximal transition portion 44B is bounded by beveled edge 52B and distal square edge 53B, distal transition portion 64B is bounded by beveled edge 72A and proximal square edge 73A, and proximal transition portion 64B is bounded by beveled edge 72B and distal square edge 73B. Between respective beveled edges 52, 72, and respective square edges 53, 73, this beveled portion is not continuous parallel to a respective axis 41, 61.

Referring to both FIG. 4A and FIG. 4B, lengths 48A, 48B, 50, 68A, 68B, and 70 of the respective portions 44A, 44B, 46, 64A, 64B, 60, may be selected such that, when a second layer including a plurality of sleeves 60 overlaps a first layer including a plurality of sleeves 40, a core portion 46 of each sleeve 40 radially overlaps with at least one transition portion 64 of a sleeve 60, and a core portion 66 of each sleeve 60 radially overlaps at least one transition portion 44 of a sleeve 40. Lengths 48, 50, 68, and 70 may include, but are not limited to, a range between about 5 millimeters and 50 millimeters, such as between 15 mm and 30 mm. In some examples, lengths 48, 50, 68, and 70 may be based on outer diameters 56, 76 of sleeves 40, 60, respectively. For example, lengths 48, 50, 68, and 70 may be between 5 and 10 times a respective outer diameter 56, 76, such as about 7 times.

In some examples, lengths 58, 78 of respective sleeves 40, 60 forming a respective layer are substantially the same within the layer. For example, each sleeve 40, 60 forming a layer may have similar dimensions, such that a durometer profile may be configured through selection of the durometer of each sleeve in the layer. In some examples, length 50 of core portion 46 is substantially the same as lengths 68 of transition portion 64, and/or lengths 48 of transition portions 44 are substantially the same as lengths 70 of core portion 66. For example, in a two layer configuration, each sleeve 40, 60 may form an entire core region of a layer and two halves of a transition region of a layer, in which the core region is substantially the same length as the transition region.

In some examples, overall lengths 58, 78 and/or lengths 48, 50, 68, and 70 are varied for different sleeves 40, 60 along an axis of the portion of the catheter. For example, a layer may have different lengths of core regions and transitions regions, such as to produce smaller changes in durometer over a particular length. The particular layer may be formed from a first set sleeves that have a first set of dimensions (e.g., lengths 48, 50, 58, 68, 70, 78) for a first portion of the outer jacket that has a smaller change in durometer and a second set of sleeves that have a second set of dimensions for a second portion of the outer jacket that has a larger change in durometer.

While sleeves 40, 60 of FIGS. 4A and 4B are configured for a two-layer outer jacket configuration, in some examples, sleeves are configured for an outer jacket having more than two layers. Such sleeves may have different lengths of core and transition portions and angles of interfacing surfaces to produce radially overlapping transitions between the layers. For example, an outer jacket that includes three layers may have a core portion that is twice as long as a transition portion, such that each transition portion of a sleeve of one layer radially overlaps two core portions of sleeves of the two other layers.

In some examples, angles 54, 74 are selected to reduce deviations in outer jacket that may form at interfaces between adjacent sleeves 40, 60. For example, angles 54, 74 that are too sharp (i.e., low) may produce an overhang that is not structurally stable or is difficult to accurately align with an adjacent sleeve. As such, in some examples, angles 54, 74 may be limited to angles greater than or equal to about 10°. In some examples, angles 54, 74 are selected to accommodate a length or change in durometer of a corresponding outer jacket formed from sleeves 40, 60. For example, angles 54, 74 may be relatively large for short devices in which a large change in durometer may occur over a short distance.

Figure 5A:
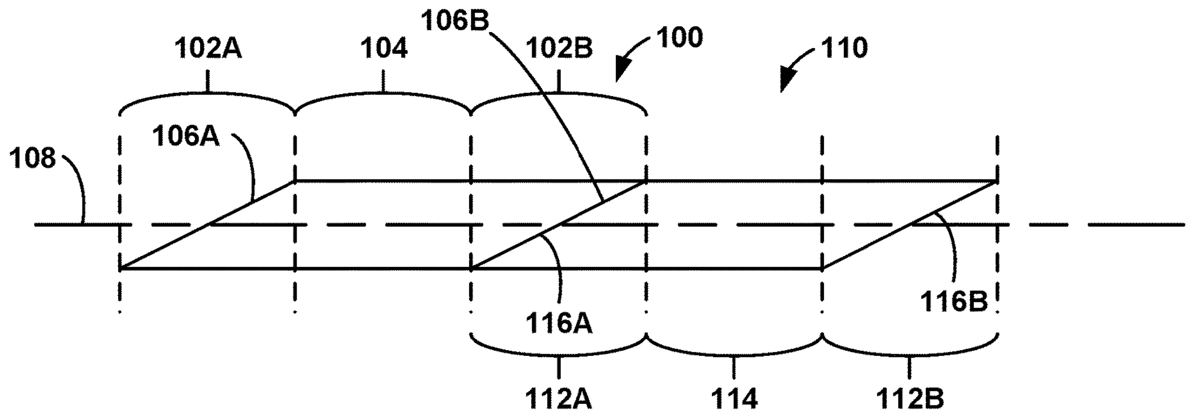
FIG. 5A is a conceptual side view of two segments of an example first layer of an outer jacket of a catheter body.
Figure 5B:
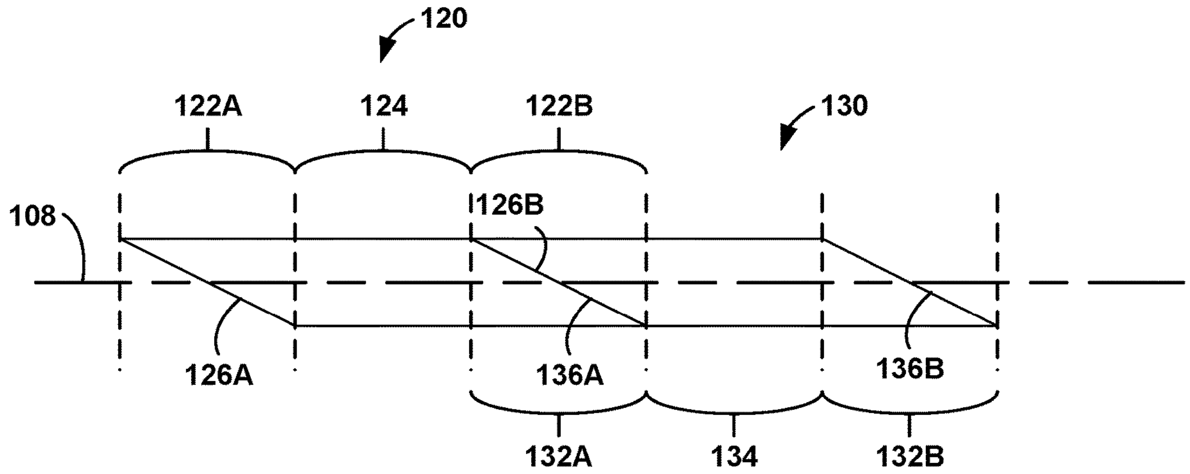
FIG. 5B is a conceptual side view of two segments of an example second layer of an outer jacket of a catheter body.

Sleeves, such as sleeves 40, 60 described in FIGS. 4A and 4B, may be longitudinally arranged to form layers of an outer jacket. FIG. 5A is a conceptual side view of two example segments of a first layer of an outer jacket of an elongated body formed from sleeves, such as sleeve 40 described in FIG. 4A, while FIG. 5B is a conceptual side view of two example segments of a second layer of the outer jacket of the elongated body formed from sleeves, such as sleeve 60 described in FIG. 4B. The elongated body defines a longitudinal axis 108.

Referring to FIG. 5A, the first layer includes a first segment 100 and a second segment 110. First segment 100 includes a first proximal transition portion 102A that is not continuous parallel to longitudinal axis 108, a first distal transition portion 102B that is not continuous parallel to longitudinal axis 108, and a first core portion 104 that is continuous parallel to longitudinal axis 108. First proximal transition portion 102A includes a first proximal beveled edge 106A and first distal transition portion 102B includes a first distal beveled edge 106B. Second segment 110 includes a second proximal transition portion 112A that is not continuous parallel to longitudinal axis 108, a second distal transition portion 112B that is not continuous parallel to longitudinal axis 108, and a second core portion 114 that is continuous parallel to longitudinal axis 108. Second proximal transition portion 112A includes a second proximal beveled edge 116A and second distal transition portion 112B includes a second distal beveled edge 116B. Second segment 110 is longitudinally adjacent to first segment 100, such that first distal beveled edge 106B of first distal transition portion 102B interfaces with second proximal beveled edge 116A of second transition portion 112A.

Referring to FIG. 5B, the second layer is overlying the first layer and includes a third segment 120 and a fourth segment 130. Third segment 120 includes a third proximal transition portion 122A that is not continuous parallel to longitudinal axis 108, a third distal transition portion 122B that is not continuous parallel to longitudinal axis 108, and a third core portion that is continuous parallel to the longitudinal axis. Third proximal transition portion 122A includes a third proximal beveled edge 126A and third distal transition portion 122B includes a third distal beveled edge 126B. Fourth segment 130 is longitudinally adjacent to third segment 120 and includes a fourth proximal transition portion 132A that is not continuous parallel to longitudinal axis 108, a fourth distal transition portion 132B that is not continuous parallel to longitudinal axis 108, and a fourth core portion 134 that is continuous parallel to longitudinal axis 108. Fourth proximal transition portion 132A includes a fourth proximal beveled edge 136A and fourth distal transition portion 132B includes a fourth distal beveled edge 136B. Fourth segment 130 is longitudinally adjacent to third segment 120, such that third distal beveled edge 126B of third distal transition portion 122B interfaces with fourth proximal beveled edge 136A of fourth transition portion 132A.

Forming the first layer includes positioning a first sleeve corresponding to first segment 100 over an inner liner, positioning a second sleeve corresponding to second segment 110 over the inner liner and longitudinally adjacent to the first sleeve, and heating the first sleeve and the second sleeve to reflow the first sleeve and the second sleeve and form the first layer of the outer jacket. Forming the second layer includes positioning a third sleeve corresponding to third segment 120 over the first layer, positioning a fourth sleeve corresponding to fourth segment 130 over the first layer and longitudinally adjacent to the third sleeve, and heating the third sleeve and the fourth sleeve to reflow the third sleeve and the fourth sleeve and form the second layer of the outer jacket. When the second layer is overlying the first layer, second core portion 114 overlaps third distal transition portion 122B and fourth proximal transition portion 132A radially from longitudinal axis 108, and third core portion 124 overlaps first distal transition portion 102B and second proximal transition portion 112A radially from longitudinal axis 108.

Figure 6:
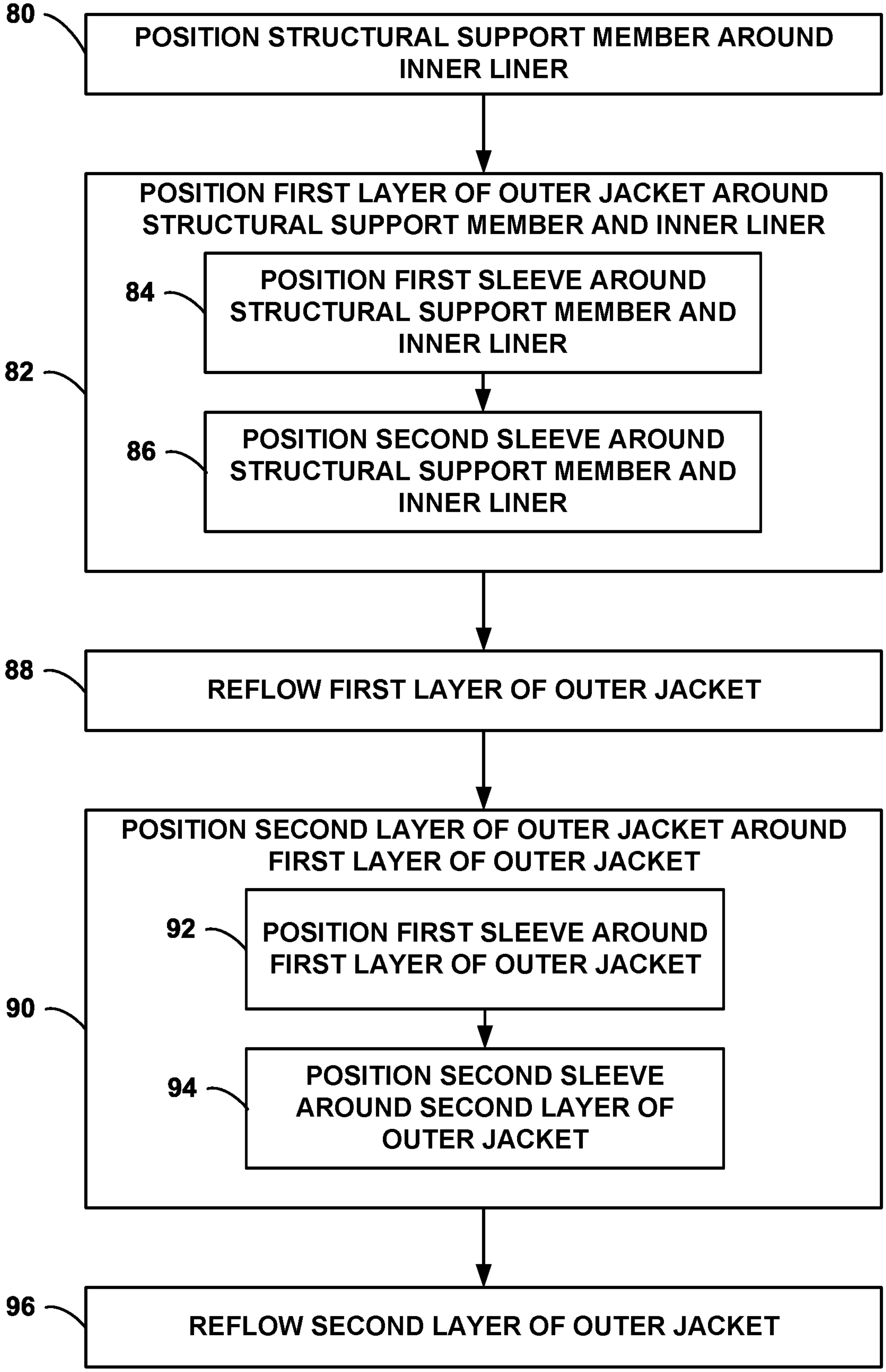
FIG. 6 is a flow diagram of an example method of forming the catheters of FIGS. 1-5.

The catheters described herein can be formed using any suitable technique. FIG. 6 is a flow diagram of an example method of forming the catheters of FIGS. 1-3, such as catheter 10 of FIGS. 1 and 2, and/or portion 30 of FIG. 3A, and will be described with reference to portion 30 of FIG. 3A, using outer jacket segments, such as segments 32, 34 of FIG. 3A and/or sleeves 40, 60 of FIGS. 4A and 4B. FIG. 6 will be described with reference to portion 30 of catheter body 12 of FIG. 3A.

At any time prior to positioning structural support member 20 over inner liner 18 (80), inner liner 18 may be positioned over a mandrel (not shown). In some examples, inner liner 18 may be positioned over the mandrel by at least inserting the mandrel through an end of inner liner 18. After positioning inner liner 18 over the mandrel, structural support member 20 may be positioned over inner liner 18 (80). In examples in which structural support member 20 includes a coil member, the wire defining the coil member may be wound over an outer surface of inner liner 18 or pushed over inner liner 18. Structural support member 20 may be secured in place relative to inner liner 18 using any suitable technique. In some examples, outer jacket 24 may at least partially secure structural support member 20 to inner liner 18.

In some examples, an adhesive and/or a polymer, such as support layer 22, may be used to secure structural support member 20 to inner liner 18. As noted above, in some examples, catheter body 12 includes support layer 22. To form support layer 22, a layer of a thermoplastic or a thermoset polymer may be applied over structural support member 20 after structural support member 20 is positioned over inner liner 18, while in other examples, a layer of a thermoplastic or a thermoset polymer may be applied over inner liner 18 prior to positioning structural support member 20 over inner liner 18. The thermoset or thermoplastic polymer may be, for example, a viscoelastic thermoset polyurethane (e.g., Flexobond 430). At least some of the polymer may be positioned between the turns of the wire defining member 20.

Positioning the thermoset or thermoplastic polymer over inner liner 18 and structural support member 20 in this manner may help bond inner liner 18 and structural support member 20 to outer jacket 24 through support layer 22. For example, the polymer may contact surfaces of structural support member 20 and provide a surface for bonding to outer jacket 24. In contrast, depositing a polymer over inner liner 18 prior to positioning structural support member 20 may lead to surfaces of structural support member 20 void of the polymer, where such surfaces may not as readily or strongly bond with outer jacket 24 as surfaces of support layer 22. After the polymer is positioned over inner liner 18 and structural support member 20, the polymer is cured (not shown), e.g., by heating and/or time-curing. In other examples, the polymer can be cured after outer jacket 24 is positioned over inner liner 18, structural support member 20, and the polymer.

After structural support member 20 is positioned over inner liner 18 (80), outer jacket 24 is positioned over an outer surface of structural support member 20 (82, 88, 90, 96). In the example of FIGS. 3 and 5, outer jacket 24 includes a first layer 26 and a second layer 28 radially outwards of first layer 26. During and/or after positioning of each layer of outer jacket 24, material of outer jacket 24 may be flowed and/or reflowed between structures (e.g., coils or braids) of structural support member 20, such that at least a portion of a volume between the structures of structural support member 20 may be filled with the material of outer jacket 24. In some instances, the material of outer jacket 24 may contact inner liner 18 to form an interface between inner liner 18 and outer jacket 24. This interface may provide adhesion between inner liner 18 and outer jacket 24, in addition to adhesion between structural support member 20 and inner liner 18 or outer jacket 24. Regardless of whether inner liner 18 and outer jacket 24 form an interface, outer jacket 24 may provide longitudinal support for structural support member 20, such that outer jacket 24 may at least partially limit movement of structural support member 20 between inner liner 18 and outer jacket 24. In this way, outer jacket 24 may assist in integrating structural support member 20 into catheter body 12.

In some examples, outer jacket 24 is adhered to an outer surface of structural support member 20, e.g., an adhesive and/or a polymer may be applied to outer surface of member 20 prior to positioning outer jacket 24 over member 20 and then cured after outer jacket 24 is positioned over member 20. In addition to, or instead of, the adhesive, outer jacket 24 may be heat shrunk over member 20 and inner liner 18. In some examples, the heat shrinking of outer jacket 24 helps secure member 20 in place relative to inner liner 18.

Outer jacket 24 includes a plurality of outer jacket segments 34, such that positioning outer jacket 24 over structural support member 20 and inner liner 18 may include positioning a plurality of sleeves around structural support member 20 and inner liner 18. For example, each sleeve may be slid over the outer surface of member 20 and positioned longitudinally adjacent to at least one other sleeve. Each sleeve of the plurality of sleeves may correspond to one or more outer jacket segments 34. The sleeves may have different compositions and/or properties. For example, at least two sleeves may have different materials, different durometers, and/or different thicknesses. In some examples, a sequence in which the sleeves may be positioned may define increasing or decreasing flexibility of catheter body 12. As one example, to increase flexibility from a proximal to a distal end of portion 30, a durometer of a first sleeve is greater than a durometer of the second sleeve, such that a durometer of first outer jacket segment 34A is greater than a durometer of second outer jacket segment 34B. As another example, to decrease flexibility from a proximal to a distal end of portion 30, a durometer of first sleeve is less than a durometer of the second sleeve, such that a durometer of first outer jacket segment 34A is less than a durometer of second outer jacket segment 34B.

In some examples, outer jacket 24 includes multiple layers as described herein at portions of the catheter that may be subject to relatively high deformation. For example, a first portion of structural support member 20 near distal opening 13 may be adjacent to a relatively low durometer section of outer jacket 24 that is more compressible. During navigation of catheter 10 through vasculature, the first portion may experience a relatively high amount of deformation that may cause delamination or detachment of outer jacket 24 from structural support member 20. Thus, the portion may include an outer jacket having a smooth durometer gradient help compensate for the stresses that may cause delamination or detachment of outer jacket 24 from structural support member 20.

In the example of FIG. 6, to position outer jacket 24, first layer 26 is positioned around structural support member 20 and inner liner 18 (82). Positioning first layer 26 may include positioning a first sleeve corresponding to first outer jacket segment 32A over structural support member 20 (84) and positioning a second sleeve corresponding to second outer jacket segment 32B over structural support member 20, distal to the first sleeve (86). After positioning outer jacket segments 32, outer jacket segments 32 may be mechanically connected together at junctions between segments 32 and configured to substantially conform to the outer surface of structural support member 20, inner liner 18, and/or a support layer (not shown) using any suitable technique. In the example of FIG. 6, mechanically connecting segments 32 involves reflowing segments 32 of first layer 26 of outer jacket 24 (88). In some examples, segments 32 are formed from a flowable/reflowable material. Heat may be applied to segments 32 to cause at least a portion of segments 32 to melt and flow into spaces between structures of structural support member 20. The heat may cause segments 32 to at least partly fuse together to define a substantially continuous first layer 26 of outer jacket 24. The use of heat to apply outer jacket 24 to the subassembly including inner liner 18 and structural support member 20 may help eliminate the need for an adhesive and/or support layer between structural support member 20 and first layer 26 of outer jacket 24.

In some examples, segments 32 are formed from a heat shrinkable material. A heat shrink tube may be positioned over segments 32 and heat may be applied to cause the heat shrink tube to wrap tightly around segments 32. The heat and wrapping force may cause segments 32 to fuse together to define a substantially continuous outer jacket 24. The heat shrunk tube may then be removed from the assembly, e.g., via skiving or any suitable technique. For example, the use of heat shrinking to apply first layer 26 of outer jacket 24 to the subassembly including inner liner 18, a support layer (optional and not shown), and structural support member 20 may help eliminate the need for an adhesive between structural support member 20 and outer jacket 24. This may help minimize the wall thickness of catheter body 12 and, therefore, increase the inner diameter of catheter body 12 for a given outer diameter. In addition, the absence of an adhesive layer adhering structural support member 20 to outer jacket 24 may contribute to an increased flexibility of catheter body 12.

In the examples of FIG. 6, once first layer 26 has been positioned over structural support member 20, and segments 32 mechanically connected to form first layer 26, second layer 28 is positioned around first layer 26 (80). Positioning second layer 28 may include positioning a first sleeve corresponding to first outer jacket segment 34A over first layer 26 (92) and positioning a second sleeve corresponding to second outer jacket segment 34B over first layer 26, distal to the first sleeve (94). The first and second sleeves may be positioned such that a core region 38 of each sleeve radially overlaps a transition region 37 of a segment 32 of first layer 26 and/or a transition region 39 of each sleeve radially overlaps a core region 36 of a segment 32 of first layer 26. For example, the second sleeve may be positioned so that a distal transition region of the second sleeve (e.g., corresponding to transition region 39A in FIG. 3C) radially overlaps core region 36A of first layer 26, a core region of the second sleeve (e.g., corresponding to core region 38A in FIG. 3C) radially overlaps a transition region 37A of first layer 26, and a proximal transition region of the second sleeve (e.g., corresponding to transition region 39B in FIG. 3C) radially overlaps core region 36B of first layer 26.

After positioning outer jacket segments 34, outer jacket segments 34 may be mechanically connected together at junctions between segments 34 and configured to substantially conform to the outer surface of first layer 26 using any suitable technique. In the example of FIG. 6, mechanically connecting segments 34 involves reflowing segments 34 of second layer 28 of outer jacket 24 (96), such as described in step 88 above.

In some examples, as will be described with reference to FIG. 1 unless otherwise indicated, a method of using catheter 10 includes introducing catheter 10 into vasculature (e.g., an intracranial blood vessel) of a patient via an access point (e.g., a femoral artery or a radial artery), and guiding catheter body 12 through the vasculature. In some instances, catheter body 12 may encounter tortuous vasculature that exerts a bending or compressive force on catheter body 12 in response to a pushing or rotating force at a proximal end of catheter 10. As catheter body 12 is advanced through the tortuous vasculature, catheter body 12 may resist kinking or buckling. As one example, as illustrated in FIG. 2, structural support member 20 may remain adhered to outer jacket 24 and/or inner liner 18, at least partly due to increased smoothness of a transition in stiffness of outer jacket 24. In this way, catheter body 12 may be increase flexibility and/or pushability of catheter 10 through tortuous vasculature of a patient. Any of the examples of catheter body 12 characteristics that contribute to a resistance to kinking or buckling can be used in combination with each other.

Once distal end 12B of catheter body 12 is positioned at the target tissue site, which may be proximal to thromboembolic material (e.g., a thrombus), the thromboembolic material be removed from the vasculature via catheter body 12. For example, the thromboembolic material may be aspirated from the vasculature by at least applying a vacuum force to inner lumen 25 of catheter body 12 via hub 14 (and/or proximal end 12A), which may cause the thromboembolic material to be introduced into inner lumen 25 via distal opening 13. Optionally, the vacuum or aspiration can be continued to thereby draw the thromboembolic material proximally along the inner lumen 25, all or part of the way to the proximal end 12A or hub 14. As a further option, the aspiration or vacuum may cause the thromboembolic material to attach or adhere to the distal tip; in such a case the catheter 10 or catheter body 12 and the thromboembolic material can be withdrawn from the vasculature together as a unit, for example through another catheter that surrounds the catheter 10 or catheter body 12.

As another example, the thromboembolic material may be removed from the vasculature using another technique, such as via an endovascular retrieval device delivered through the inner lumen 25 of the catheter body 12. In such a method the catheter body 12 can be inserted into the vasculature (for example using any technique disclosed herein) and the retrieval device advanced through the inner lumen 25 (or through another catheter, such as a microcatheter, inserted into the vasculature through the inner lumen 25) so that the device engages the thromboembolic material. The retrieval device and the material engaged thereby (together with any other catheter or microcatheter) can then be retracted into the inner lumen 25 and removed from the patient. Optionally, aspiration can be performed with or through the catheter body 12 during retraction of the retrieval device and thromboembolic material into the catheter body 12. The vasculature can comprise the neurovasculature, peripheral vasculature or cardiovasculature. The thromboembolic material may be located using any suitable technique, such as fluoroscopy, intravascular ultrasound or carotid Doppler imaging techniques.

This disclosure includes the following non-limiting examples.

Example 1: A catheter includes an elongated body defining a longitudinal axis and includes a first layer includes a first segment, wherein the first segment comprises a first transition portion that is not continuous parallel to the longitudinal axis and a first core portion that is continuous parallel to the longitudinal axis; and a second segment longitudinally adjacent to the first segment, wherein the second segment comprises a second transition portion that is not continuous parallel to the longitudinal axis and a second core portion that is continuous parallel to the longitudinal axis; and a second layer overlying the first layer and includes a third segment, wherein the third segment comprises a third transition portion that is not continuous parallel to the longitudinal axis and a third core portion that is continuous parallel to the longitudinal axis; and a fourth segment longitudinally adjacent to the third segment, wherein the fourth segment comprises a fourth transition portion that is not continuous parallel to the longitudinal axis and a fourth core portion that is continuous parallel to the longitudinal axis, wherein the second core portion overlaps the third and fourth transition portions radially from the longitudinal axis, and wherein the third core portion overlaps the first and second transition portions radially from the longitudinal axis.

Example 2: The catheter of example 1, wherein a first beveled edge of the first transition portion interfaces with a second beveled edge of the second transition portion, and wherein a third beveled edge of the third transition portion interfaces with a fourth beveled edge of the fourth transition portion.

Example 3: The catheter of example 2, wherein each of the first core portion, the second core portion, the third core portion, and the fourth core portion is defined by a tubular portion of the respective segment, and wherein each of the first transition portion, the second transition portion, the third transition portion, and the fourth transition portion is defined by a beveled portion of the respective segment.

Example 4: The catheter of any of examples 1 through 3, wherein the first segment comprises a proximal transition portion proximal to the first core portion and a distal transition portion distal to the first core portion.

Example 5: The catheter of any of examples 1 through 4, wherein a length of the first core portion and a length of the first transition portion are substantially the same.

Example 6: The catheter of any of examples 1 through 5, wherein each of the first segment, the second segment, the third segment, and the fourth segment defines a shape from a side profile orthogonal to the axis comprising at least one of a parallelogram or a trapezium.

Example 7: The catheter of any of examples 1 through 6, wherein a length of the second core portion and a length of the third transition portion are substantially the same.

Example 8: The catheter of any of examples 1 through 7, wherein the outer jacket comprises a third layer overlying the second layer and includes a fifth segment, wherein the fifth segment comprises a fifth transition portion that is not continuous parallel to the longitudinal axis and a fifth core portion that is continuous parallel to the longitudinal axis; and a sixth segment longitudinally adjacent to the fifth segment, wherein the sixth segment comprises a sixth transition portion that is not continuous parallel to the longitudinal axis and a sixth core portion that is continuous parallel to the longitudinal axis, wherein the fifth core portion overlaps the third and fourth transition portions.

Example 9: The catheter of example 8, wherein a length of the first core region is different from a length of the first transition portion.

Example 10: The catheter of any of examples 1 through 9, wherein each of the first segment, the second segment, the third segment, and the fourth segment have a uniform durometer within the respective segment.

Example 11: The catheter of any of examples 1 through 10, wherein the first segment defines a different durometer than the second segment, and wherein the third segment defines a different durometer than the fourth segment.

Example 12: The catheter of any of examples 1 through 11, wherein an average of a durometer of the first layer and a durometer of the second layer decreases from a proximal end of the outer jacket to a distal end of the outer jacket.

Example 13: The catheter of any of examples 1 through 12, wherein a durometer of the first layer decreases from a proximal end of the first layer to a distal end of the first layer, and wherein a durometer of the second layer decreases from a proximal end of the second layer to a distal end of the second layer.

Example 14: The catheter of any of examples 1 through 13, wherein a durometer of the first outer jacket segment is greater than a durometer of the second outer jacket segment.

Example 15: The catheter of any of examples 1 through 14, wherein a durometer of the first outer jacket segment is less than a durometer of the second outer jacket segment.

Example 16: The catheter of any of examples 1 through 15, wherein the elongated body further comprises: an inner liner defining an inner lumen of the elongated body; and a structural support member positioned between at least a portion of the inner liner and the outer jacket, wherein the structural support member is configured to provide longitudinal support to the elongated body along the longitudinal axis, and wherein the structural support member comprises at least one of a coiled structural support member or a braided structural support member.

Example 17: The catheter of any of examples 1 through 16, wherein the first layer defines a first durometer gradient along the longitudinal axis that includes alternating regions of a uniform durometer and a transition in durometer, wherein the second layer defines a second durometer gradient along the longitudinal axis that includes alternating regions of a uniform durometer and a transition in durometer, and wherein the first durometer gradient and the second durometer gradient define a smooth durometer gradient along the longitudinal axis of the portion of the outer jacket.

Example 18: The catheter of example 17, wherein the first durometer gradient comprises a change in durometer of the first layer along the longitudinal axis, wherein the second durometer gradient comprises a change in durometer of the second layer along the longitudinal axis, and wherein the smooth durometer gradient comprises a change in durometer along the longitudinal axis that does not include a step change.

Example 19: A method includes forming an elongated body of a catheter, the elongated body defining an axis, wherein forming the elongated body comprises positioning an outer jacket over an inner liner, the inner liner defining an inner lumen of the elongated body, and wherein the outer jacket comprises: a first layer includes a first segment, wherein the first segment comprises a first transition portion that is not continuous parallel to the longitudinal axis and a first core portion that is continuous parallel to the longitudinal axis; and a second segment longitudinally adjacent to the first segment, wherein the second segment comprises a second transition portion that is not continuous parallel to the longitudinal axis and a second core portion that is continuous parallel to the longitudinal axis; and a second layer overlying the first layer and includes a third segment, wherein the third segment comprises a third transition portion that is not continuous parallel to the longitudinal axis and a third core portion that is continuous parallel to the longitudinal axis; and a fourth segment longitudinally adjacent to the third segment, wherein the fourth segment comprises a fourth transition portion that is not continuous parallel to the longitudinal axis and a fourth core portion that is continuous parallel to the longitudinal axis, wherein the second core portion overlaps the third and fourth transition portions radially from the longitudinal axis, and wherein the third core portion overlaps the first and second transition portions radially from the longitudinal axis.

Example 20: The method of example 19, wherein positioning the outer jacket over the inner liner comprises: positioning a first sleeve over the inner liner, wherein the first sleeve corresponds to the first segment; positioning a second sleeve over the inner liner and longitudinally adjacent to the first sleeve, wherein the second sleeve corresponds to the second segment; heating the first sleeve and the second sleeve to reflow the first sleeve and the second sleeve and form the first layer of the outer jacket; positioning a third sleeve over the first layer, wherein the third sleeve corresponds to the third segment; positioning a fourth sleeve over the first layer and longitudinally adjacent to the third sleeve, wherein the fourth sleeve corresponds to the fourth segment; and heating the third sleeve and the fourth sleeve to reflow the third sleeve and the fourth sleeve and form the second layer of the outer jacket.

Various aspects of the disclosure have been described. These and other aspects are within the scope of the following claims.

What is claimed is:

1. A catheter, comprising:

an elongated body defining a longitudinal axis and comprising an outer jacket, wherein a portion of the outer jacket comprises:

a first layer comprising:

a first segment, wherein the first segment comprises a first transition portion that is not continuous parallel to the longitudinal axis and a first core portion that is continuous parallel to the longitudinal axis; and a second segment longitudinally adjacent to the first segment, wherein the second segment comprises a second transition portion that is not continuous parallel to the longitudinal axis and a second core portion that is continuous parallel to the longitudinal axis; and a second layer overlying the first layer and comprising:

a third segment, wherein the third segment comprises a third transition portion that is not continuous parallel to the longitudinal axis and a third core portion that is continuous parallel to the longitudinal axis; and a fourth segment longitudinally adjacent to the third segment, wherein the fourth segment comprises a fourth transition portion that is not continuous parallel to the longitudinal axis and a fourth core portion that is continuous parallel to the longitudinal axis, wherein the second core portion overlaps the third and fourth transition portions radially from the longitudinal axis, and wherein the third core portion overlaps the first and second transition portions radially from the longitudinal axis.

2. The catheter of claim 1, wherein a first beveled edge of the first transition portion interfaces with a second beveled edge of the second transition portion, and wherein a third beveled edge of the third transition portion interfaces with a fourth beveled edge of the fourth transition portion.

3. The catheter of claim 2, wherein each of the first core portion, the second core portion, the third core portion, and the fourth core portion is defined by a tubular portion of the respective segment, and wherein each of the first transition portion, the second transition portion, the third transition portion, and the fourth transition portion is defined by a beveled portion of the respective segment.

4. The catheter of claim 1, wherein the first segment comprises a proximal transition portion proximal to the first core portion and a distal transition portion distal to the first core portion.

5. The catheter of claim 1, wherein a length of the first core portion and a length of the first transition portion are substantially the same.

6. The catheter of claim 1, wherein each of the first segment, the second segment, the third segment, and the fourth segment defines a shape from a side profile orthogonal to the longitudinal axis comprising at least one of a parallelogram or a trapezium.

7. The catheter of claim 1, wherein a length of the second core portion and a length of the third transition portion are substantially the same.

8. The catheter of claim 1, wherein the outer jacket comprises a third layer overlying the second layer and comprising:

a fifth segment, wherein the fifth segment comprises a fifth transition portion that is not continuous parallel to the longitudinal axis and a fifth core portion that is continuous parallel to the longitudinal axis; and a sixth segment longitudinally adjacent to the fifth segment, wherein the sixth segment comprises a sixth transition portion that is not continuous parallel to the longitudinal axis and a sixth core portion that is continuous parallel to the longitudinal axis, wherein the fifth core portion overlaps the third and fourth transition portions.

9. The catheter of claim 8, wherein a length of the first core portion is different from a length of the first transition portion.

10. The catheter of claim 1, wherein each of the first segment, the second segment, the third segment, and the fourth segment have a uniform durometer within the respective segment.

11. The catheter of claim 1, wherein the first segment defines a different durometer than the second segment, and wherein the third segment defines a different durometer than the fourth segment.

12. The catheter of claim 1, wherein an average of a durometer of radially adjacent materials of the first layer and a durometer of the second layer decreases from a proximal end of the outer jacket to a distal end of the outer jacket.

13. The catheter of claim 1, wherein a durometer of the first layer decreases from a proximal end of the first layer to a distal end of the first layer, and wherein a durometer of the second layer decreases from a proximal end of the second layer to a distal end of the second layer.

14. The catheter of claim 1, wherein a durometer of the first segment of the outer jacket is greater than a durometer of the second segment of the outer jacket.

15. The catheter of claim 1, wherein a durometer of the first segment of the outer jacket is less than a durometer of the second segment of the outer jacket.

16. The catheter of claim 1, wherein the elongated body further comprises:

an inner liner defining an inner lumen of the elongated body; and a structural support member positioned between at least a portion of the inner liner and the outer jacket, wherein the structural support member is configured to provide longitudinal support to the elongated body along the longitudinal axis, and wherein the structural support member comprises at least one of a coiled structural support member or a braided structural support member.

17. The catheter of claim 1, wherein the first layer defines a first durometer gradient along the longitudinal axis that includes alternating regions of a uniform durometer and a transition in durometer, wherein the second layer defines a second durometer gradient along the longitudinal axis that includes alternating regions of a uniform durometer and a transition in durometer, and wherein the first durometer gradient and the second durometer gradient define a smooth durometer gradient along the longitudinal axis of the portion of the outer jacket.

18. The catheter of claim 17, wherein the first durometer gradient comprises a change in durometer of the first layer along the longitudinal axis, wherein the second durometer gradient comprises a change in durometer of the second layer along the longitudinal axis, and wherein the smooth durometer gradient comprises a change in durometer along the longitudinal axis that does not include a step change.

19. A method, comprising:

forming an elongated body of a catheter, the elongated body defining a longitudinal axis, wherein forming the elongated body comprises positioning an outer jacket over an inner liner, the inner liner defining an inner lumen of the elongated body, and wherein the outer jacket comprises:

a first layer comprising:

a first segment, wherein the first segment comprises a first transition portion that is not continuous parallel to the longitudinal axis and a first core portion that is continuous parallel to the longitudinal axis; and a second segment longitudinally adjacent to the first segment, wherein the second segment comprises a second transition portion that is not continuous parallel to the longitudinal axis and a second core portion that is continuous parallel to the longitudinal axis; and a second layer overlying the first layer and comprising:

a third segment, wherein the third segment comprises a third transition portion that is not continuous parallel to the longitudinal axis and a third core portion that is continuous parallel to the longitudinal axis; and a fourth segment longitudinally adjacent to the third segment, wherein the fourth segment comprises a fourth transition portion that is not continuous parallel to the longitudinal axis and a fourth core portion that is continuous parallel to the longitudinal axis, wherein the second core portion overlaps the third and fourth transition portions radially from the longitudinal axis, and wherein the third core portion overlaps the first and second transition portions radially from the longitudinal axis.

20. The method of claim 19, wherein positioning the outer jacket over the inner liner comprises:

positioning a first sleeve over the inner liner, wherein the first sleeve corresponds to the first segment;

positioning a second sleeve over the inner liner and longitudinally adjacent to the first sleeve, wherein the second sleeve corresponds to the second segment;

heating the first sleeve and the second sleeve to reflow the first sleeve and the second sleeve and form the first layer of the outer jacket;

positioning a third sleeve over the first layer, wherein the third sleeve corresponds to the third segment;

positioning a fourth sleeve over the first layer and longitudinally adjacent to the third sleeve, wherein the fourth sleeve corresponds to the fourth segment; and heating the third sleeve and the fourth sleeve to reflow the third sleeve and the fourth sleeve and form the second layer of the outer jacket.

* * * * *